United States Patent
Reboul et al.

(10) Patent No.: US 10,583,619 B2
(45) Date of Patent: Mar. 10, 2020

(54) PROCESS FOR MANUFACTURING AN INTRAOCULAR LENS WITH AN EMBEDDED MASK

(71) Applicant: AcuFocus, Inc., Irvine, CA (US)

(72) Inventors: Adam C. Reboul, Sarasota, FL (US); Patrick H. Benz, Sarasota, FL (US); R. Kyle Webb, Carlsbad, CA (US)

(73) Assignee: AcuFocus, Inc., Irvine, CA (US)

( * ) Notice: Subject to any disclaimer, the term of this patent is extended or adjusted under 35 U.S.C. 154(b) by 0 days.

(21) Appl. No.: 16/250,392

(22) Filed: Jan. 17, 2019

(65) Prior Publication Data

US 2019/0315081 A1    Oct. 17, 2019

Related U.S. Application Data

(60) Continuation of application No. 15/815,017, filed on Nov. 16, 2017, now Pat. No. 10,183,453, which is a
(Continued)

(51) Int. Cl.
*B29D 11/02* (2006.01)
*B29C 33/12* (2006.01)
(Continued)

(52) U.S. Cl.
CPC .............. *B29D 11/023* (2013.01); *A61F 2/16* (2013.01); *B29C 33/123* (2013.01);
(Continued)

(58) Field of Classification Search
CPC .............. B29D 11/023; B29D 11/0048; B29D 11/00442; B29K 2995/0093;
(Continued)

(56) References Cited

U.S. PATENT DOCUMENTS 2,350,421 A    6/1944   Schoder et al.
2,470,927 A    5/1949   Hale, Jr.
(Continued)

FOREIGN PATENT DOCUMENTS

AU    2004201751    5/2004
CN    1875895       12/2006
(Continued)

OTHER PUBLICATIONS

Internet Archive Wayback Machine; Aniridia Implants; downloaded from https://web.archive.org/web/20110824062840/http://www.morcher.com/nc/produkte/aniridiaimplants.html (Archived Aug. 24, 2011; printed on Feb. 5, 2015).
(Continued)

*Primary Examiner* — Nahida Sultana
(74) *Attorney, Agent, or Firm* — Knobbe Martens Olson & Bear, LLP

(57) ABSTRACT

Intraocular implants and methods of making intraocular implants are provided. The intraocular implant can include a mask adapted to increase depth of focus. The method of manufacturing the implant can include positioning the mask with an aperture on a protruding pin of a positioning mold portion. The protruding pin can be configured to center the mask in the intraocular lens.

18 Claims, 10 Drawing Sheets

Related U.S. Application Data continuation of application No. 15/427,456, filed on Feb. 8, 2017, now Pat. No. 9,844,919, which is a continuation of application No. 15/133,139, filed on Apr. 19, 2016, now Pat. No. 9,573,328, which is a division of application No. 13/830,889, filed on Mar. 14, 2013, now Pat. No. 9,427,922.

(51) Int. Cl.
  *B29D 11/00* (2006.01)
  *A61F 2/16* (2006.01)
  *B29K 627/12* (2006.01)

(52) U.S. Cl.
  CPC .... *B29D 11/0048* (2013.01); *B29D 11/00442* (2013.01); *A61F 2002/1681* (2013.01); *A61F 2230/0006* (2013.01); *B29K 2627/16* (2013.01); *B29K 2995/0093* (2013.01)

(58) Field of Classification Search
  CPC .................. B29K 2627/16; A61F 2/16; A61F 2002/1681; A61F 2230/0006; B29C 33/123
  See application file for complete search history.

(56) References Cited

U.S. PATENT DOCUMENTS

| | | |
|---|---|---|
| 3,034,403 A | 5/1962 | Neefe |
| 3,270,099 A | 8/1966 | Camp |
| 3,458,870 A | 8/1969 | Stone |
| 3,578,850 A | 5/1971 | Grant |
| 3,776,230 A | 12/1973 | Neefe |
| 3,794,414 A | 2/1974 | Wesley |
| 3,877,502 A | 4/1975 | Hunckler |
| 3,996,627 A | 12/1976 | Deeg et al. |
| 4,010,496 A | 3/1977 | Neefe |
| 4,104,338 A | 8/1978 | Guerrieri |
| 4,116,439 A | 9/1978 | Chavarria et al. |
| 4,210,391 A | 7/1980 | Cohen |
| 4,298,996 A | 11/1981 | Barnet |
| 4,340,283 A | 7/1982 | Cohen |
| 4,402,579 A | 9/1983 | Poler |
| 4,423,728 A | 1/1984 | Lieberman |
| 4,435,050 A | 3/1984 | Poler |
| 4,450,593 A | 5/1984 | Poler |
| 4,505,855 A | 3/1985 | Bruns et al. |
| 4,563,565 A | 1/1986 | Kampfer et al. |
| 4,575,373 A | 3/1986 | Johnson |
| 4,596,578 A | 6/1986 | Kelman |
| 4,607,617 A | 8/1986 | Choyce |
| 4,624,669 A | 11/1986 | Grendahl |
| 4,639,105 A | 1/1987 | Neefe |
| 4,646,720 A | 3/1987 | Peyman et al. |
| 4,655,774 A | 4/1987 | Choyce |
| 4,665,913 A | 5/1987 | Esperance, Jr. |
| 4,669,466 A | 6/1987 | L'Esperance |
| 4,669,834 A | 6/1987 | Richter |
| 4,676,790 A | 6/1987 | Kern |
| 4,676,791 A | 6/1987 | LeMaster et al. |
| 4,678,422 A | 7/1987 | York |
| 4,701,038 A | 10/1987 | Neefe |
| 4,715,858 A | 12/1987 | Lindstrom |
| 4,767,647 A | 8/1988 | Bree |
| 4,795,462 A | 1/1989 | Grendahl |
| 4,798,608 A | 1/1989 | Grendahl |
| 4,799,784 A | 1/1989 | Safir |
| 4,799,931 A | 1/1989 | Lindstrom |
| 4,807,623 A | 2/1989 | Lieberman |
| 4,813,955 A | 3/1989 | Achatz et al. |
| 4,815,690 A | 3/1989 | Shepherd |
| 4,817,789 A | 4/1989 | Paul |
| 4,830,855 A | 5/1989 | Stewart |
| 4,842,599 A | 6/1989 | Bronstein |
| 4,842,782 A | 6/1989 | Portney |
| 4,851,003 A | 7/1989 | Lindstrom |
| 4,863,466 A | 9/1989 | Schlegel |
| 4,881,860 A | 11/1989 | Kanazawa |
| 4,903,695 A | 2/1990 | Warner et al. |
| 4,907,586 A | 3/1990 | Bille et al. |
| 4,928,815 A | 5/1990 | Paul |
| 4,955,904 A | 9/1990 | Atebara et al. |
| 4,976,732 A | 12/1990 | Vorosmarthy |
| 4,994,080 A | 2/1991 | Shepard |
| 5,013,319 A | 5/1991 | Davis |
| 5,030,230 A | 7/1991 | White |
| 5,034,166 A | 7/1991 | Rawlings et al. |
| 5,041,133 A | 8/1991 | Sayano et al. |
| 5,055,602 A | 10/1991 | Melpolder |
| 5,087,015 A | 2/1992 | Galley |
| 5,090,955 A | 2/1992 | Simon |
| 5,094,521 A | 3/1992 | Jolson et al. |
| 5,098,443 A | 3/1992 | Parel et al. |
| 5,108,427 A | 4/1992 | Majercik et al. |
| 5,112,328 A | 5/1992 | Taboada et al. |
| 5,120,120 A | 6/1992 | Cohen |
| 5,120,121 A | 6/1992 | Rawlings et al. |
| 5,137,441 A | 8/1992 | Fogarty |
| 5,147,395 A * | 9/1992 | Willis ............... A61F 2/1613 623/6.4 |
| 5,171,318 A | 12/1992 | Gibson et al. |
| 5,185,107 A | 2/1993 | Blake |
| 5,188,494 A | 2/1993 | Hatin |
| 5,192,316 A | 3/1993 | Ting |
| 5,196,026 A | 3/1993 | Barrett et al. |
| 5,213,749 A | 5/1993 | Huss et al. |
| 5,260,727 A | 11/1993 | Oksman et al. |
| 5,266,241 A | 11/1993 | Parekh |
| 5,269,795 A | 12/1993 | Arnott |
| 5,269,812 A | 12/1993 | White |
| 5,274,404 A | 12/1993 | Michael |
| 5,288,436 A | 2/1994 | Liu et al. |
| 5,290,892 A | 3/1994 | Namdaran et al. |
| 5,292,514 A | 3/1994 | Capecchi et al. |
| 5,300,116 A | 4/1994 | Chirila et al. |
| 5,312,330 A | 5/1994 | Klopotek |
| 5,314,439 A | 5/1994 | Sugita |
| 5,314,961 A | 5/1994 | Anton et al. |
| 5,332,802 A | 7/1994 | Kelman et al. |
| 5,336,261 A | 8/1994 | Barrett et al. |
| 5,354,331 A | 10/1994 | Schachar et al. |
| 5,358,520 A | 10/1994 | Patel |
| 5,372,580 A | 12/1994 | Simon et al. |
| 5,391,201 A | 2/1995 | Barrett et al. |
| 5,441,511 A | 8/1995 | Hanna |
| 5,474,548 A | 12/1995 | Knopp et al. |
| 5,507,740 A | 4/1996 | O'Donnell, Jr. |
| 5,547,468 A | 4/1996 | Simon et al. |
| D375,245 S | 11/1996 | Irving |
| 5,578,080 A | 11/1996 | McDonald |
| 5,603,774 A | 2/1997 | LeBoeuf et al. |
| 5,607,437 A | 3/1997 | Simon et al. |
| 5,624,456 A | 4/1997 | Hellenkamp |
| 5,627,613 A | 5/1997 | Kaneko |
| 5,628,794 A | 5/1997 | Lindstrom |
| 5,628,795 A | 5/1997 | Langerman |
| 5,647,865 A | 7/1997 | Swinger |
| 5,653,752 A | 8/1997 | Silvestrini et al. |
| 5,662,706 A | 9/1997 | Legerton et al. |
| 5,674,284 A | 10/1997 | Chang et al. |
| 5,693,268 A | 12/1997 | Widman et al. |
| 5,697,923 A | 12/1997 | Poler |
| 5,702,440 A | 12/1997 | Portney |
| 5,708,049 A | 1/1998 | Katagiri et al. |
| 5,713,957 A | 2/1998 | Steele et al. |
| 5,722,971 A | 3/1998 | Peyman |
| 5,725,575 A | 3/1998 | O'Donnell, Jr. |
| 5,746,558 A | 5/1998 | Nygren et al. |
| 5,752,967 A | 5/1998 | Kritzinger et al. |
| 5,757,458 A | 5/1998 | Miller et al. |
| 5,769,889 A | 6/1998 | Kelman |
| 5,774,202 A | 6/1998 | Abraham et al. |
| 5,786,883 A | 7/1998 | Miller et al. |

(56) References Cited

U.S. PATENT DOCUMENTS

| | | | |
|---|---|---|---|
| 5,824,086 A | 10/1998 | Silvestrini |
| 5,837,156 A | 11/1998 | Cumming |
| 5,843,105 A | 12/1998 | Mathis et al. |
| 5,864,128 A | 1/1999 | Plesko |
| 5,870,167 A | 2/1999 | Knopp et al. |
| 5,895,610 A | 4/1999 | Chang et al. |
| 5,905,561 A | 5/1999 | Lee et al. |
| 5,910,537 A | 6/1999 | Feingold et al. |
| 5,913,898 A | 6/1999 | Feingold et al. |
| 5,919,185 A | 7/1999 | Peyman |
| 5,925,294 A | 7/1999 | Shibuya |
| 5,964,748 A | 10/1999 | Peyman |
| 5,964,776 A | 10/1999 | Peyman |
| 5,965,330 A | 10/1999 | Evans et al. |
| 5,980,040 A | 11/1999 | Xu et al. |
| 6,017,121 A | 1/2000 | Chateau et al. |
| 6,063,073 A | 5/2000 | Peyman |
| 6,090,141 A | 7/2000 | Lindstrom |
| 6,102,946 A | 8/2000 | Nigam |
| 6,106,553 A | 8/2000 | Feingold et al. |
| 6,110,166 A | 8/2000 | Juhasz et al. |
| 6,138,307 A | 10/2000 | McDonald |
| 6,152,959 A | 11/2000 | Portney |
| 6,164,777 A | 12/2000 | Li et al. |
| 6,171,336 B1 | 1/2001 | Sawusch |
| 6,178,593 B1 | 1/2001 | Carlson |
| 6,197,019 B1 | 3/2001 | Peyman |
| 6,201,036 B1 | 3/2001 | Fedorov et al. |
| 6,203,538 B1 | 3/2001 | Peyman |
| 6,210,401 B1 | 4/2001 | Lai |
| 6,217,571 B1 | 4/2001 | Peyman |
| 6,217,596 B1 | 4/2001 | Farah |
| 6,221,067 B1 | 4/2001 | Peyman |
| 6,228,113 B1 | 5/2001 | Kaufman |
| 6,228,114 B1 | 5/2001 | Lee |
| 6,228,115 B1 | 5/2001 | Hoffmann et al. |
| 6,264,648 B1 | 7/2001 | Peyman |
| 6,277,146 B1 | 8/2001 | Peyman et al. |
| 6,280,470 B1 | 8/2001 | Peyman |
| 6,280,471 B1 | 8/2001 | Peyman et al. |
| 6,302,877 B1 | 10/2001 | Ruiz |
| 6,304,390 B1 | 10/2001 | Takanashi |
| 6,308,590 B1 | 10/2001 | Berto |
| 6,335,190 B1 | 1/2002 | Zhou et al. |
| 6,361,560 B1 | 3/2002 | Nigam |
| 6,376,153 B2 | 4/2002 | Uchikawa et al. |
| 6,387,379 B1 | 5/2002 | Goldberg et al. |
| 6,391,230 B1 | 5/2002 | Sarbadhikari |
| 6,416,179 B1 | 7/2002 | Lieberman et al. |
| 6,423,093 B1 | 7/2002 | Hicks et al. |
| 6,432,246 B1 | 8/2002 | Blake |
| 6,436,092 B1 | 8/2002 | Peyman |
| 6,458,141 B1 | 10/2002 | Peyman |
| 6,461,384 B1 | 10/2002 | Hoffmann et al. |
| 6,469,844 B1 | 10/2002 | Iwase et al. |
| 6,480,346 B2 | 11/2002 | Funakoshi |
| 6,491,637 B2 | 12/2002 | Foster et al. |
| 6,497,700 B1 | 12/2002 | LaHaye |
| 6,515,006 B2 | 2/2003 | Horn |
| 6,551,307 B2 | 4/2003 | Peyman |
| 6,554,424 B1 | 4/2003 | Miller et al. |
| 6,554,860 B2 | 4/2003 | Hoffmann et al. |
| 6,555,103 B2 | 4/2003 | Leukel et al. |
| 6,575,573 B2 | 6/2003 | Lai et al. |
| 6,581,993 B2 | 6/2003 | Nigam |
| 6,588,902 B2 | 7/2003 | Isogai |
| 6,589,280 B1 | 7/2003 | Koziol |
| 6,607,527 B1 | 8/2003 | Ruiz et al. |
| 6,613,088 B1 | 9/2003 | Babizhayev |
| 6,638,304 B2 | 10/2003 | Azar |
| 6,649,722 B2 | 11/2003 | Rosenzweig et al. |
| 6,655,804 B2 | 12/2003 | Streibig |
| 6,692,126 B1 | 2/2004 | Xie et al. |
| 6,702,807 B2 | 3/2004 | Peyman |
| 6,726,322 B2 | 4/2004 | Andino et al. |
| 6,740,116 B2 | 5/2004 | Morcher |
| 6,755,858 B1 | 6/2004 | White |
| 6,786,926 B2 | 9/2004 | Peyman |
| 6,811,256 B1 | 11/2004 | Becherer et al. |
| 6,855,163 B2 | 2/2005 | Peyman |
| 6,874,886 B2 | 4/2005 | Miller et al. |
| 6,899,424 B2 | 5/2005 | Miller et al. |
| 6,949,093 B1 | 9/2005 | Peyman |
| 6,951,556 B2 | 10/2005 | Epstein |
| 6,966,648 B2 | 11/2005 | Miller et al. |
| 6,989,008 B2 | 1/2006 | Peyman |
| 6,997,428 B1 * | 2/2006 | Andino ............ B29D 11/00432 249/134 |
| 7,001,374 B2 | 2/2006 | Peyman |
| 7,008,447 B2 | 3/2006 | Koziol |
| 7,025,455 B2 | 4/2006 | Roffman |
| 7,061,693 B2 | 6/2006 | Zalevsky |
| 7,099,057 B2 | 8/2006 | Parker et al. |
| 7,276,080 B2 | 10/2007 | Murakami et al. |
| 7,287,852 B2 | 10/2007 | Fiala |
| 7,364,674 B1 | 4/2008 | Hoover |
| 7,399,811 B2 | 7/2008 | Mentak et al. |
| 7,404,637 B2 | 7/2008 | Miller et al. |
| 7,404,638 B2 | 7/2008 | Miller et al. |
| 7,446,157 B2 | 11/2008 | Mentak et al. |
| 7,455,404 B2 | 11/2008 | Bandhauer et al. |
| 7,455,691 B2 | 11/2008 | Feingold et al. |
| 7,462,193 B2 | 12/2008 | Nagamoto |
| 7,477,452 B2 | 1/2009 | Tsuruma |
| 7,491,350 B2 | 1/2009 | Silvestrini |
| 7,497,866 B2 | 3/2009 | Perez |
| 7,628,810 B2 | 12/2009 | Christie et al. |
| 7,641,337 B2 | 1/2010 | Altmann |
| 7,645,299 B2 | 1/2010 | Koziol |
| 7,745,555 B2 | 6/2010 | Mentak et al. |
| 7,842,367 B2 | 11/2010 | Mentak |
| 7,976,577 B2 | 7/2011 | Silvestrini |
| D645,337 S | 9/2011 | Hsu et al. |
| 8,043,371 B2 | 10/2011 | Paul et al. |
| 8,048,972 B2 | 11/2011 | Mentak et al. |
| 8,079,706 B2 | 12/2011 | Silvestrini et al. |
| D656,526 S | 3/2012 | Christie et al. |
| 8,157,374 B2 | 4/2012 | Bandhauer et al. |
| 8,241,354 B2 | 8/2012 | Hong et al. |
| 8,287,592 B2 | 10/2012 | Silvestrini |
| 8,343,215 B2 | 1/2013 | Miller et al. |
| D681,086 S | 4/2013 | Christie et al. |
| 8,420,753 B2 | 4/2013 | Mentak et al. |
| 8,460,374 B2 | 6/2013 | Christie et al. |
| 8,604,098 B2 | 12/2013 | Boydston et al. |
| 8,740,978 B2 | 6/2014 | Weeber et al. |
| 8,752,958 B2 | 6/2014 | Miller et al. |
| 8,633,292 B2 | 7/2014 | Hu et al. |
| 8,858,624 B2 | 10/2014 | Christie et al. |
| 8,864,824 B2 | 10/2014 | Silvestrini et al. |
| 8,955,968 B2 | 2/2015 | Zalevsky et al. |
| 9,005,281 B2 | 4/2015 | Christie et al. |
| 9,138,142 B2 | 9/2015 | Christie et al. |
| 9,204,962 B2 | 12/2015 | Silvestrini |
| 9,427,311 B2 | 8/2016 | Christie et al. |
| 9,427,922 B2 | 8/2016 | Reboul et al. |
| 9,492,272 B2 | 11/2016 | Christie et al. |
| 9,545,303 B2 | 1/2017 | Vilupuru et al. |
| 9,573,328 B2 | 2/2017 | Reboul et al. |
| 9,603,704 B2 | 3/2017 | Silvestrini |
| 9,757,227 B2 | 9/2017 | Kushlin et al. |
| 9,844,919 B2 | 12/2017 | Reboul et al. |
| 9,848,979 B2 | 12/2017 | Vilupuru et al. |
| 9,943,403 B2 | 4/2018 | Webb et al. |
| 9,987,127 B2 | 6/2018 | Bogaert et al. |
| 10,183,453 B2 | 1/2019 | Reboul et al. |
| 2001/0027314 A1 | 10/2001 | Peyman |
| 2001/0034516 A1 | 10/2001 | Peyman |
| 2001/0050750 A1 | 12/2001 | Breger |
| 2002/0010510 A1 | 1/2002 | Silverstrini |
| 2002/0082288 A1 | 6/2002 | Horn |
| 2002/0120329 A1 | 8/2002 | Lang et al. |
| 2002/0167640 A1 | 11/2002 | Francis et al. |
| 2002/0196409 A1 | 12/2002 | Jani |

(56) References Cited

U.S. PATENT DOCUMENTS

| | | |
|---|---|---|
| 2003/0014042 A1 | 1/2003 | Juhasz et al. |
| 2003/0105521 A1 | 6/2003 | Perez |
| 2003/0135272 A1 | 7/2003 | Brady et al. |
| 2003/0149480 A1 | 8/2003 | Shadduck |
| 2003/0204258 A1 | 10/2003 | Graham et al. |
| 2003/0216763 A1 | 11/2003 | Patel |
| 2004/0019379 A1 | 1/2004 | Glick et al. |
| 2004/0056371 A1 | 3/2004 | Liao et al. |
| 2004/0068317 A1 | 4/2004 | Knight |
| 2004/0106929 A1 | 6/2004 | Masket |
| 2004/0140578 A1 | 7/2004 | Kelly et al. |
| 2005/0027355 A1 | 2/2005 | Murakami et al. |
| 2005/0046794 A1 | 3/2005 | Silvestrini et al. |
| 2005/0056954 A1 | 3/2005 | Devlin |
| 2005/0090895 A1 | 4/2005 | Peyman |
| 2005/0124983 A1 | 6/2005 | Frey et al. |
| 2005/0134793 A1 | 6/2005 | Roffman |
| 2005/0137703 A1 | 6/2005 | Chen |
| 2005/0143751 A1 | 6/2005 | Makker et al. |
| 2005/0182488 A1 | 8/2005 | Peyman |
| 2005/0187621 A1 | 8/2005 | Brady |
| 2005/0288784 A1 | 12/2005 | Peyman |
| 2006/0064077 A1 | 3/2006 | Peyman |
| 2006/0079959 A1 | 4/2006 | Christie et al. |
| 2006/0113054 A1 | 6/2006 | Silvestrini |
| 2006/0184243 A1 | 8/2006 | Yilmaz |
| 2006/0232665 A1 | 10/2006 | Schowengerdt et al. |
| 2006/0235428 A1 | 10/2006 | Silvestrini |
| 2006/0235514 A1 | 10/2006 | Silvestrini |
| 2006/0241751 A1 | 10/2006 | Marmo et al. |
| 2006/0265058 A1 | 11/2006 | Silvestrini |
| 2006/0268226 A1 | 11/2006 | Christie et al. |
| 2006/0268227 A1 | 11/2006 | Christie et al. |
| 2006/0268228 A1 | 11/2006 | Christie et al. |
| 2006/0268229 A1 | 11/2006 | Silvestrini et al. |
| 2006/0270946 A1 | 11/2006 | Silvestrini et al. |
| 2006/0271026 A1 | 11/2006 | Silvestrini et al. |
| 2006/0271178 A1 | 11/2006 | Christie et al. |
| 2006/0271179 A1 | 11/2006 | Christie et al. |
| 2006/0271180 A1 | 11/2006 | Christie et al. |
| 2006/0271181 A1 | 11/2006 | Christie et al. |
| 2006/0271182 A1 | 11/2006 | Christie et al. |
| 2006/0271183 A1 | 11/2006 | Christie et al. |
| 2006/0271184 A1 | 11/2006 | Silvestrini |
| 2006/0271185 A1 | 11/2006 | Silvestrini |
| 2006/0274264 A1 | 12/2006 | Christie et al. |
| 2006/0274265 A1 | 12/2006 | Christie et al. |
| 2007/0032866 A1 | 2/2007 | Portney |
| 2007/0091472 A1 | 4/2007 | Alkemper et al. |
| 2007/0092592 A1 | 4/2007 | Chiang |
| 2007/0129797 A1 | 6/2007 | Lang et al. |
| 2007/0225691 A1 | 9/2007 | Silvestrini et al. |
| 2008/0306587 A1 | 12/2008 | Your |
| 2009/0012505 A1 | 1/2009 | Chernyak |
| 2009/0021692 A1 | 1/2009 | Miller et al. |
| 2009/0287306 A1 | 1/2009 | Smith et al. |
| 2009/0059168 A1 | 3/2009 | Miller et al. |
| 2009/0069817 A1 | 3/2009 | Peyman |
| 2009/0171458 A1 | 7/2009 | Kellan et al. |
| 2009/0204207 A1 | 8/2009 | Blum et al. |
| 2009/0222086 A1 | 9/2009 | Lui et al. |
| 2009/0234448 A1 | 9/2009 | Weeber et al. |
| 2009/0306773 A1 | 12/2009 | Silvestrini et al. |
| 2010/0082100 A1 | 4/2010 | Mikawa |
| 2010/0127412 A1 | 5/2010 | Lake |
| 2010/0149618 A1 | 6/2010 | Sprague |
| 2010/0312336 A1 | 12/2010 | Hong et al. |
| 2011/0037184 A1 | 2/2011 | Shoji et al. |
| 2011/0040376 A1* | 2/2011 | Christie ............... A61F 2/1613 623/6.17 |
| 2011/0051080 A1 | 3/2011 | Bandhauer et al. |
| 2011/0125261 A1 | 5/2011 | Portney |
| 2011/0166652 A1 | 7/2011 | Bogaert et al. |
| 2011/0172675 A1 | 7/2011 | Danta et al. |
| 2011/0245919 A1 | 10/2011 | Pettit |
| 2011/0251685 A1 | 10/2011 | Chu |
| 2012/0203239 A1 | 8/2012 | Vukich et al. |
| 2012/0245683 A1 | 9/2012 | Christie et al. |
| 2012/0309761 A1 | 12/2012 | Chow et al. |
| 2012/0310338 A1 | 12/2012 | Christie et al. |
| 2013/0053953 A1 | 2/2013 | Silvestrini |
| 2013/0131795 A1 | 5/2013 | Miller et al. |
| 2013/0147072 A1 | 6/2013 | Bothe et al. |
| 2013/0238091 A1 | 9/2013 | Danta et al. |
| 2013/0289543 A1 | 10/2013 | Mordaunt |
| 2014/0131905 A1 | 5/2014 | Webb |
| 2014/0379078 A1 | 12/2014 | Trindade |
| 2015/0025627 A1 | 1/2015 | Christie et al. |
| 2015/0073549 A1 | 3/2015 | Webb et al. |
| 2015/0177422 A1 | 6/2015 | Liu et al. |
| 2015/0183173 A1 | 7/2015 | Linhardt et al. |
| 2015/0366658 A1 | 12/2015 | Christie et al. |
| 2016/0297107 A1 | 10/2016 | Shim et al. |
| 2017/0049560 A1 | 2/2017 | Cherne |
| 2017/0143477 A1 | 5/2017 | Christie et al. |
| 2017/0156850 A1 | 6/2017 | Silvestrini et al. |
| 2018/0125639 A1 | 5/2018 | Vilupuru et al. |
| 2018/0296322 A1 | 10/2018 | Webb et al. |
| 2018/0338826 A1 | 11/2018 | Link et al. |
| 2019/0076235 A1 | 3/2019 | Webb et al. |
| 2019/0076241 A1 | 3/2019 | Alarcon Heredia et al. |
| 2019/0193350 A1* | 6/2019 | Gu .................... B29D 11/0048 |

FOREIGN PATENT DOCUMENTS

| | | |
|---|---|---|
| CN | 100368846 | 2/2008 |
| CN | 101322663 | 12/2008 |
| CN | 101341426 B | 7/2012 |
| DE | 4134320 | 4/1992 |
| EP | 0165652 | 12/1985 |
| EP | 0443094 | 8/1991 |
| EP | 1173790 | 1/2002 |
| EP | 1674049 | 6/2006 |
| EP | 1548489 B1 | 8/2006 |
| EP | 2319457 | 5/2011 |
| EP | 2243052 B1 | 9/2011 |
| EP | 2365379 | 9/2011 |
| EP | 2455799 | 5/2012 |
| EP | 2823789 | 1/2015 |
| EP | 2364457 B1 | 8/2015 |
| FR | 2620687 | 3/1989 |
| FR | 2649605 | 1/1991 |
| GB | 1276003 | 6/1972 |
| JP | 62-167343 | 7/1987 |
| JP | 64-002644 | 1/1989 |
| JP | H02-7954 | 1/1990 |
| JP | 04-158859 | 6/1992 |
| JP | 06-509731 | 3/1993 |
| JP | H05-65340 | 9/1993 |
| JP | 06-502782 | 3/1994 |
| JP | H07-067896 | 3/1995 |
| JP | 07-265340 | 10/1995 |
| JP | 08-103457 A | 4/1996 |
| JP | H09-502542 | 3/1997 |
| JP | 11-503657 | 8/1997 |
| JP | 07-178125 | 7/1998 |
| JP | 2000-047145 | 2/2000 |
| JP | 2002-537895 | 11/2002 |
| JP | 2003-502109 | 1/2003 |
| JP | 2004-510199 | 4/2004 |
| JP | 2004-538034 | 12/2004 |
| JP | 2005-533576 | 11/2005 |
| JP | 2007-516794 | 6/2007 |
| JP | 2007-523720 | 8/2007 |
| JP | 2008-506710 | 3/2008 |
| JP | S59-54527 | 5/2008 |
| KR | 10-0335722 | 5/2002 |
| RU | 2138837 | 9/1999 |
| SU | 1380743 A1 | 3/1988 |
| WO | WO 87/05797 | 10/1987 |
| WO | WO 95/03747 | 2/1995 |
| WO | WO 95/08135 | 3/1995 |
| WO | WO 96/35397 | 11/1996 |
| WO | WO 98/48715 | 11/1998 |

(56) References Cited

FOREIGN PATENT DOCUMENTS

| | | |
|---|---|---|
| WO | WO 00/025704 | 5/2000 |
| WO | WO 00/038594 | 7/2000 |
| WO | WO 00/51682 | 9/2000 |
| WO | WO 00/52516 | 9/2000 |
| WO | WO 00/70388 | 11/2000 |
| WO | WO 2001/010641 | 2/2001 |
| WO | WO 01/15779 | 3/2001 |
| WO | WO 01/17460 | 3/2001 |
| WO | WO 01/19364 | 3/2001 |
| WO | WO 01/082815 | 11/2001 |
| WO | WO 02/076320 | 10/2002 |
| WO | WO 02/102241 | 12/2002 |
| WO | WO 03/020177 | 3/2003 |
| WO | WO 03/022168 | 3/2003 |
| WO | WO 03/061518 | 7/2003 |
| WO | WO 2004/014969 | 2/2004 |
| WO | WO 2004/034917 | 4/2004 |
| WO | WO 2004/105588 | 12/2004 |
| WO | WO 2004/113959 | 12/2004 |
| WO | WO 2005/082265 | 9/2005 |
| WO | WO 2006/020638 | 2/2006 |
| WO | WO 2006/047534 | 5/2006 |
| WO | WO 2006/060380 | 6/2006 |
| WO | WO 2006/069012 | 6/2006 |
| WO | WO 2006/113377 | 10/2006 |
| WO | WO 2006/113411 | 10/2006 |
| WO | WO 2006/113563 | 10/2006 |
| WO | WO 2006/113564 | 10/2006 |
| WO | WO 2007/057734 | 10/2007 |
| WO | WO 2007/133384 | 11/2007 |
| WO | WO 2007/142981 | 12/2007 |
| WO | WO 2008/036671 | 3/2008 |
| WO | WO 2008/102096 | 8/2008 |
| WO | WO 2009/050511 | 4/2009 |
| WO | WO 2009/122409 | 10/2009 |
| WO | WO 2009/140080 | 11/2009 |
| WO | WO 2009/149060 | 12/2009 |
| WO | WO 2010/059214 | 5/2010 |
| WO | WO 2011/020074 | 2/2011 |
| WO | WO 2011/020078 | 2/2011 |
| WO | WO 2011/047076 | 4/2011 |
| WO | WO 2011/069059 | 6/2011 |
| WO | WO 2011/088107 | 7/2011 |
| WO | WO 2012/170066 | 12/2012 |
| WO | WO 2013/019871 | 2/2013 |
| WO | WO 2013/082545 | 6/2013 |
| WO | WO 2013/101793 | 7/2013 |
| WO | WO 2013/112589 | 8/2013 |
| WO | WO 2013/123265 | 8/2013 |
| WO | WO 2014/054946 | 4/2014 |
| WO | WO 2014/074610 | 5/2014 |
| WO | WO 2014/158653 | 10/2014 |
| WO | WO 2014/164056 | 10/2014 |
| WO | WO 2015/021323 | 2/2015 |
| WO | WO 2015/069927 | 5/2015 |
| WO | WO 2015/073718 | 5/2015 |
| WO | WO 2016/081493 | 5/2016 |
| WO | WO 2017/062316 | 4/2017 |
| WO | WO 2017/091520 | 6/2017 |
| WO | WO 2019/010178 | 1/2019 |

OTHER PUBLICATIONS

Guyton A.C., Textbook of Medical Physiology, 7th Edition, W.B. Saunders Company, Jan. 1986: Chapter 58, in 13 pages.
International Search Report and Written Opinion for PCT/US2014/019118 dated Jul. 21, 2014 in 10 pages.
Lu Xuequan, et al. "Radiation preparation and thermo-response swelling of interpenetrating polymer network hydrogel composed of PNIPAAm and PMMA", Radiation Physics and Chemistry, vol. 57, Mar. 2000, pp. 477-480, XP002473596.
Patel, C.K., et al. "Imaging the macula through a black occlusive intraocular lens". Arch. Ophthalmol. Oct. 2010; 128(10):1374-1376.
Yusuf, et al., "Inability to perform posterior segment monitoring by scanning laser ophthalmoscopy or optical coherence tomography with some occlusive intraocular lenses in clinical use", J. Cataract Refract. Surg., Mar. 2012, 38: 513-518.
Yusuf, et al., "Occlusive IOLs for Intractable Diplopia Demonstrate a Novel Near-Infrared Window of Transmission for SLO/OCT Imaging and Clinical Assessment". Investigative Ophthalmology & Visual Science, May 2011, 52(6): 3737-3743.

* cited by examiner

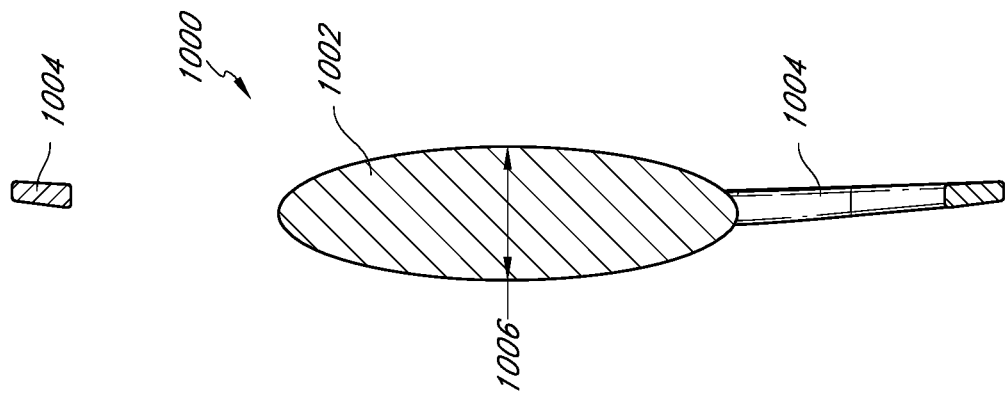
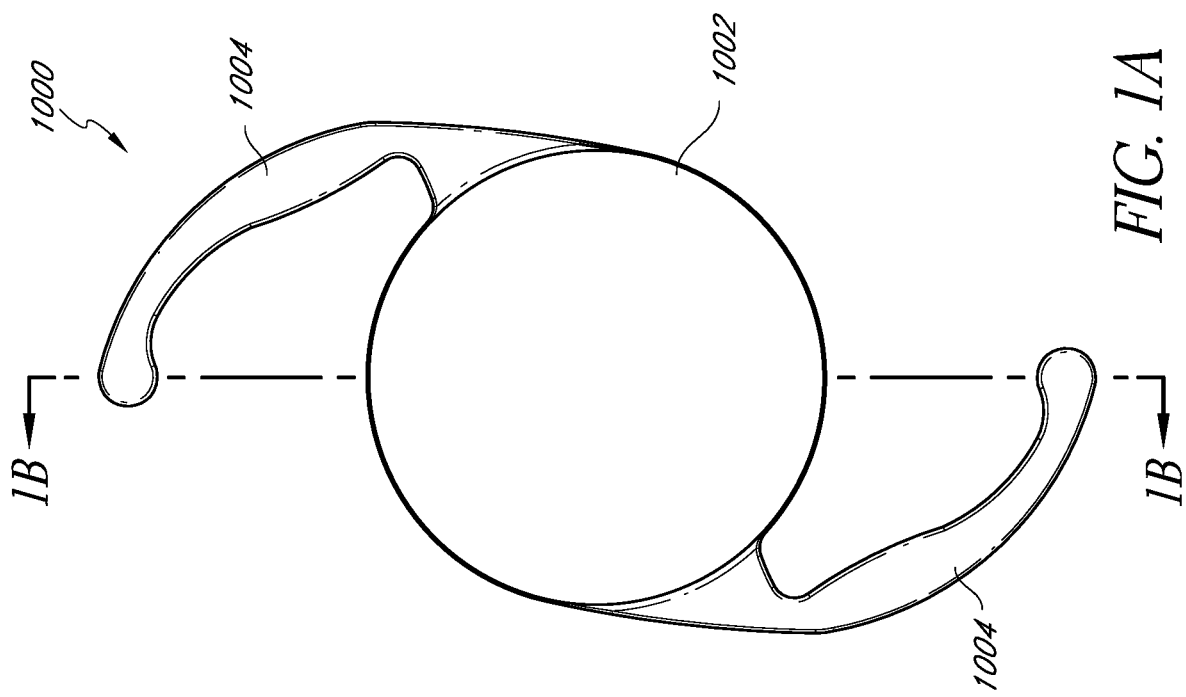
FIG. 1B
FIG. 1A

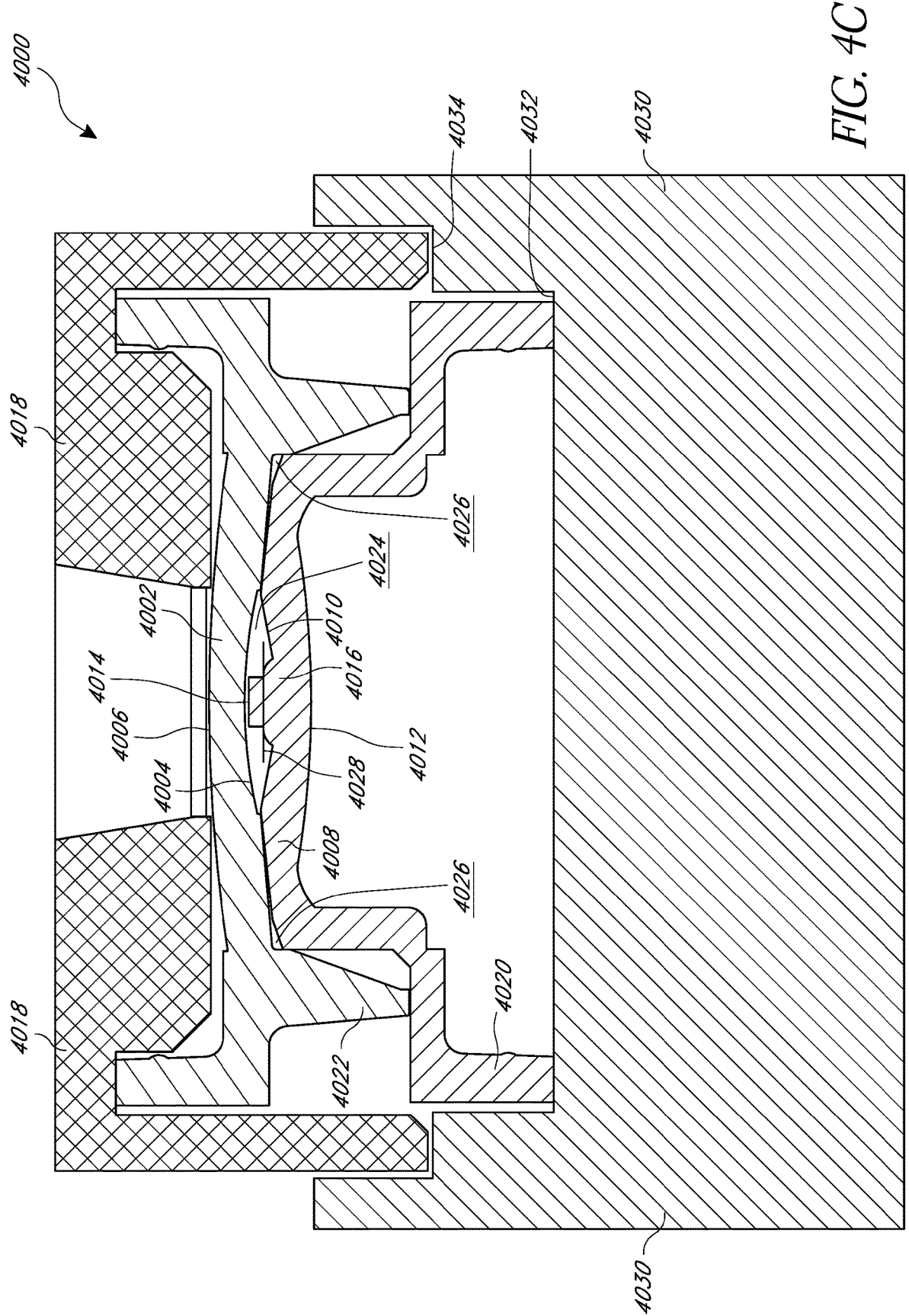

PROCESS FOR MANUFACTURING AN INTRAOCULAR LENS WITH AN EMBEDDED MASK

CROSS REFERENCE TO RELATED APPLICATIONS

This application is a continuation of U.S. patent application Ser. No. 15/815,017, filed on Nov. 16, 2017, which is a continuation of U.S. patent application Ser. No. 15/427,456, now U.S. Pat. No. 9,844,919, filed on Feb. 8, 2017, which is a continuation of U.S. patent application Ser. No. 15/133,139, now U.S. Pat. No. 9,573,328, filed on Apr. 19, 2016, which is a divisional of U.S. patent application Ser. No. 13/830,889, now U.S. Pat. No. 9,427,922, filed on Mar. 14, 2013, which is hereby incorporated by reference in its entirety.

BACKGROUND

Field

This application relates generally to the field of intraocular devices. More particularly, this application is directed to intraocular implants and lenses (IOLs) with an aperture to increase depth of focus (e.g. "masked" intraocular lenses), and methods of making the same.

Description of the Related Art

The human eye functions to provide vision by transmitting and focusing light through a clear outer portion called the cornea, and further refining the focus of the image onto a retina by way of a crystalline lens. The quality of the focused image depends on many factors including the size and shape of the eye, and the transparency of the cornea and the lens.

The optical power of the eye is determined by the optical power of the cornea and the crystalline lens. In a normal, healthy eye, sharp images of distant objects are formed on the retina (emmetropia). In many eyes, images of distant objects are either formed in front of the retina because the eye is abnormally long or the cornea is abnormally steep (myopia), or formed in back of the retina because the eye is abnormally short or the cornea is abnormally flat (hyperopia).

Some people suffer from cataracts in which the crystalline lens undergoes a loss of transparency. In such cases, the crystalline lens can be removed and replaced with an intraocular lens (IOL). However, some intraocular lenses may still leave defects in a patient's non-distance eyesight.

SUMMARY

Certain aspects of this disclosure are directed toward a method of manufacturing an intraocular lens. The method can include adding a first amount of a lens material to a first lens forming mold portion. The method can include positioning a mask with an aperture on a protruding pin of a positioning mold portion. The protruding pin can be configured to center the mask in the intraocular lens. The method can include joining the first lens forming mold portion and the positioning mold portion. The method can include partially curing the first amount of the lens material. Any of the mold features, intraocular lens or mask features, steps, or processes disclosed in this specification can be included in any embodiment.

In the above mentioned method aspect, the lens material can include an ultraviolet light absorber and a light-sensitive initiator. The initiator can be configured to cure the lens material when exposed to light having a wavelength outside the absorption spectrum of the ultraviolet light absorber. In certain aspects, the initiator can be configured to be activated by light having a wavelength in a range from about 380 nm to about 495 nm.

In any of the above mentioned method aspects, positioning the mask on the protruding pin can include positioning the mask adjacent to a shoulder portion of the protruding pin having a diameter larger than the aperture of the mask. The shoulder portion can be configured to control the depth of the mask in the intraocular lens.

In any of the above mentioned method aspects, joining the first lens forming mold portion and the positioning mold portion can cause lens material to flow into a space between a surface of the mask and an inner surface of the positioning mold portion from which the protruding pin extends so as to at least partially surround the mask with lens material on both of its sides.

In any of the above mentioned method aspects, partially curing the first amount of the lens material can include applying light to the first lens forming mold portion.

In any of the above mentioned method aspects, partially curing the first amount of the lens material can include curing the first amount of the lens material less than 50% of a full cure but to a sufficient degree that the mask remains with the first lens forming mold portion after removing the positioning mold portion.

In any of the above mentioned method aspects, the method can include cooling the first lens forming mold portion. The cooling process can help bias the mold set such that the lens material and mask remain in the first lens forming mold portion when the mold portions are separated. Other methods of biasing the mold set can include, but are not limited to, forming the first lens forming mold portion from a material that adheres to the lens material to a greater extent than the positioning mold portion material.

In any of the above mentioned method aspects, the method can include removing the positioning mold portion and joining the first lens forming mold portion and a second lens forming mold portion.

In any of the above mentioned method aspects, the method can include adding a second amount of the lens material to the second lens forming mold portion. In certain aspects, the method can include partially curing the second amount of the lens material less than 50% of a full cure by exposure to light. In certain aspects, the method can include, after partially curing the second amount of the lens material by exposure to light, thermally curing the second amount of the lens material.

In any of the above mentioned method aspects, the method can include polymerizing at least 99% of the first and second amounts of the lens material.

In any of the above mentioned method aspects, the lens material can be a hydrophobic material.

In any of the above mentioned method aspects, the method can include joining a haptic shield and the positioning mold portion such that the haptic shield prevents polymerization of the lens material in a haptic region.

Certain aspects of this disclosure are directed toward a mold set for manufacturing an intraocular lens having a mask suspended within the intraocular lens. The mold set can include a first lens forming mold portion configured to hold at least a portion of a lens material. The mold set can include a positioning mold portion configured to position the mask within the lens material. The positioning mold portion can be configured to mate with the first lens forming mold portion. The positioning mold portion can include a body portion and a protruding pin extending from the body portion. An end portion of the protruding pin can have a first diameter sized to correspond to an aperture in the mask. The protruding pin can be configured to control centration of the mask within the lens material. In certain aspects, the protruding pin can include a shoulder portion having a second diameter that is larger than the first diameter. The shoulder portion can be configured to control the depth of the mask within the lens material. Any of the mold features, intraocular lens or mask features, steps, or processes disclosed in this specification can be included in any embodiment.

In the above mentioned mold aspect, the length of the protruding pin can be sized such that the end portion of the protruding pin extends within 0 mm to 0.2 mm from the lens forming surface of the first lens forming mold portion when the positioning mold portion is joined with the first lens forming mold portion.

In any of the above mentioned mold aspects, a length of the protruding pin can be configured such that an optical zone of the intraocular lens is substantially free of the lens material when the first mold portion mates with the positioning mold portion.

In any of the above mentioned mold aspects, the second diameter of the shoulder portion can be about 50% of an outer diameter of the mask.

In any of the above mentioned mold aspects, the shoulder portion can be configured such that the lens material can flow between a surface of the mask and the body portion.

In any of the above mentioned mold aspects, the mold can include a second lens forming mold portion configured to hold another portion of the lens material and join with the first lens forming mold portion.

In any of the above mentioned mold aspects, the first lens forming mold portion can include a haptic region. In certain aspects, the mold can include a haptic shield positioned on the positioning mold portion such that the haptic shield blocks curing light from reaching the haptic region so as to prevent polymerization of the lens material within the haptic region.

For purposes of summarizing the disclosure, certain aspects, advantages and features of the inventions have been described herein. It is to be understood that not necessarily any or all such advantages are achieved in accordance with any particular embodiment of the inventions disclosed herein. No aspects of this disclosure are essential or indispensable.

BRIEF DESCRIPTION OF THE DRAWINGS

FIG. 1A illustrates a top view of an example embodiment of an intraocular lens having an embedded mask for improving depth of focus.

FIG. 1B illustrates a cross-sectional view of the intraocular lens of FIG. 1A taken along line 1B-1B.

FIGS. 4A-4D illustrate the cross-sectional views of an embodiment of a mold set.

DETAILED DESCRIPTION

Figure 2A:
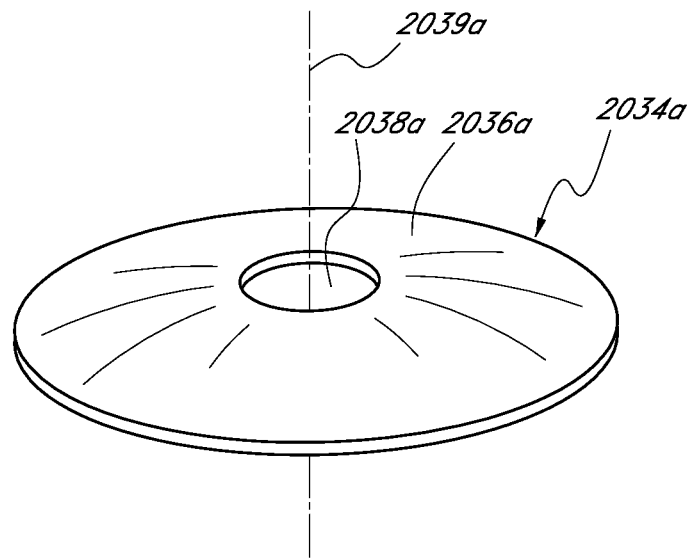
FIG. 2A is a perspective view of one embodiment of a mask configured to increase depth of focus.

As discussed herein, people who undergo intraocular lens (IOL) implantation surgery may still suffer from defects in their non-distance eyesight. One technique for treating such defects is by including a mask within the IOL that increases the patient's depth of focus. The intraocular implants of the embodiments described herein include a mask adapted to provide a small aperture for light to pass through to the retina to increase depth of focus. The light rays that pass through the mask within the IOL converge at a single focal point on the retina, while the light rays that would not converge at the single point on retina are blocked by the mask. This disclosure describes methods for manufacturing a lens, such as an IOL, having an embedded mask.

Several alternatives to fixed-focus IOLs have been developed, including multifocal IOLs and accommodating IOLs, that attempt to provide the ability to see clearly at both near and far distances. However, accommodating IOLs can be complex and some multifocal IOLs do not perform well at intermediate distances and cause glare, halos, and night vision difficulties associated with the presence of unfocused light. This limitation can force designers of multifocal optics to choose how much of the light is directed to each focal point, and to deal with the effects of the unfocused light that is always present in any image. In order to maximize acuity at the important distances of infinity (>6M) and 40 cm (normal reading distance), it is typical to provide little or no light focused at an intermediate distance, and as a result, visual acuity at these distances is poor. With a mask that includes an aperture to increase depth-of-focus, however, the intermediate vision of a patient can be improved significantly. For example, the defocus blur associated with the aperture can be less at intermediate distances than at near.

FIGS. 1A-B illustrate an example embodiment of an intraocular lens having an embedded mask 1008 for increasing depth of focus. The intraocular lens 1000 includes haptics 1004 for positioning the lens within the eye. The cross-sectional thickness of the lens body 1002 is generally dependent on the optical power of the intraocular lens 1000 and the material of the lens body 1002. In particular, the central region of the lens body 1002 is generally the thickest section of the intraocular lens 1000 with a central region cross-sectional thickness 1006. Methods for reducing the thickness of the intraocular lens are described in U.S. Pub. No. 2011/0040376, filed Aug. 13, 2010, which is hereby incorporated by reference in its entirety.

The intraocular lens and/or the lens body can be made from one or more materials. In certain embodiments, the intraocular lens material can include a hydrophobic material and/or a low-viscosity material. For example, in certain embodiments, the lens material can include a hydrophobic co-polymer such as those disclosed in U.S. Pat. No. 7,067, 602, filed Jun. 27, 2006, which is hereby incorporated by reference in its entirety. In other embodiments, the intraocular lens and/or the lens body can comprise polymers (e.g.

PMMA, PVDF, polypropylene, polycarbonate, PEEK, polyethylene, acrylic copolymers, polystyrene, PVC, polysulfone), hydrogels, or silicone.

In certain embodiments, the lens material can include an ultraviolet light absorber to provide protection for the eye. The intraocular lens body can be configured to permit less than about 10% of light transmission at 370 nm, less than about 5% of light transmission at 370 nm, less than about 1% of light transmission at 370 nm, or otherwise.

In certain embodiments, the intraocular lens can have a bi-convex design and/or can be configured to have a power range from at least about 12.5 diopter to less than or equal to about 30 diopter. In certain embodiments, the refractive index at 589 nm can be between about 1.481 and/or 1.487, between about 1.481 and/or 1.484, or otherwise. In certain embodiments, the refractive index at 546 nm can be between about 1.483 and/or 1.489, between about 1.482 and/or 1.484, or otherwise. In certain embodiments, the lens body can have a shore A hardness of at least about 90 and/or less than or equal to about 95. In certain embodiments, the lens body can have a shore A hardness of about 93.

Masks

Figure 2B:
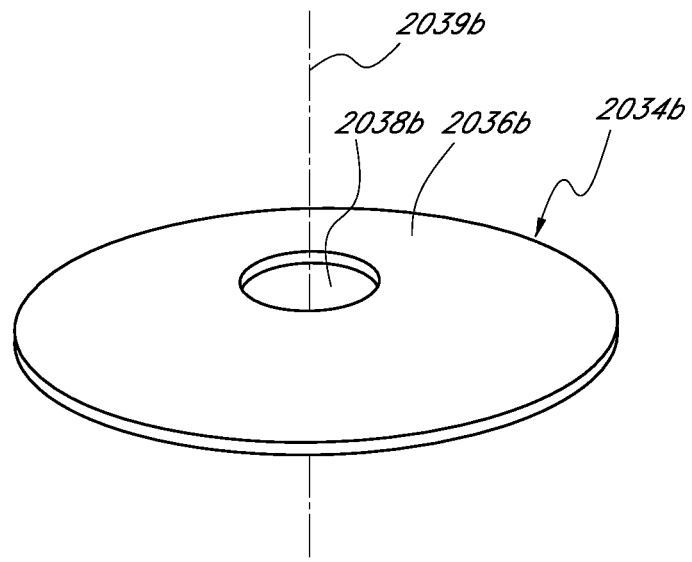
FIG. 2B is a perspective view of an embodiment of a substantially flat mask configured to increase depth of focus.

A variety of variations of masks that can be positioned on or within the implant body are discussed herein, and also described in U.S. Pat. No. 7,628,810, U.S. Patent Publication No. 2006/0113054, and U.S. Patent Publication No. 2006/0265058, all of which are hereby incorporated by reference in their entirety. FIG. 2A illustrates one embodiment of a mask 2034a. The mask 2034a can include an annular region 2036a surrounding an aperture 2038a substantially centrally located on the mask 2034a. The aperture 2038a can be generally located around a central axis 2039a, referred to herein as the optical axis of the mask 2034a. The aperture 2038a can be in the shape of a circle. FIG. 2B illustrates another embodiment of a mask 2034b similar to the mask 2034a illustrated in FIG. 2A. The annular region 2036a of the mask 2034a of FIG. 2A has a curvature from the outer periphery to the inner periphery of the annular region 2036a, while the annular region 2036b of the mask 2034b of FIG. 2B can be substantially flat.

The mask can have dimensions configured to function with the implant body to improve a patient's vision. For example, the thickness of the mask can vary depending on the location of the mask relative to the implant body. For example, if the mask is embedded within the implant body, the mask can have a thickness greater than zero and less than the thickness of the implant body. Alternatively, if the mask is coupled to a surface of the implant body, the mask may preferably have a thickness no greater than necessary to have desired opacity so that the mask does not add additional thickness to the intraocular lens.

The mask may have a constant thickness, as discussed below. However, in some embodiments, the thickness of the mask may vary between the inner periphery (near the aperture 2038a,b) and the outer periphery.

The annular region 2036a,b can be at least partially opaque or can be completely opaque. The degree of opacity of the annular region 2036a,b can prevent at least some or substantially all light from being transmitted through the mask 2034a,b. Opacity of the annular region 2036a,b can be achieved in any of several different ways.

For example, in some embodiments, the material used to make mask 2034a,b can be naturally opaque. In some embodiments, the material used to make the mask 2034a,b can be substantially clear, but treated with a dye or other pigmentation agent to render region 2036a,b substantially or completely opaque. In some embodiments, the surface of the mask 2034a,b can be treated physically or chemically (such as by etching) to alter the refractive and transmissive properties of the mask 2034a,b and make it less transmissive to light.

The material of the mask 2034a,b can be, for example, any polymeric material. Where the mask 2034a,b is applied to the intraocular implant, the material of the mask 2034a,b should be biocompatible. Examples of suitable materials for the mask 2034a,b can include, but are not limited to, highly fluorinated polymers, such as PVDF, hydrogels, or fibrous materials, such as a Dacron mesh.

In some embodiments, a photochromic material can be used as the mask or in addition to mask. Under bright light conditions, the photochromic material can darken thereby creating a mask and enhancing near vision. Under dim light conditions, the photochromic material can lighten, which allows more light to pass through to the retina. In certain embodiments, under dim light conditions, the photochromic material lightens to expose an optic of the intraocular implant. Further photochromic material details are disclosed in U.S. patent application Ser. No. 13/691,625, filed Nov. 30, 2012, which is hereby incorporated by reference in its entirety.

The mask can have different degrees of opacity. For example, the mask can block substantially all of visible light or a portion of visible light. The opacity of the mask can also vary in different regions of the mask. In certain embodiments, the opacity of the outer edge and/or the inner edge of the mask can be less than the central region of the mask. The opacity in different regions can transition abruptly or have a gradient transition. Additional examples of opacity transitions can be found in U.S. Pat. Nos. 5,662,706, 5,905,561 and 5,965,330, all of which are hereby incorporated by reference in their entirety.

Further mask details are disclosed in U.S. Pat. No. 4,976,732, issued Dec. 11, 1990, U.S. Pat. No. 7,628,810, issued Dec. 8, 2009, and in U.S. patent application Ser. No. 10/854,032, filed May 26, 2004, all of which are hereby incorporated by reference in their entirety.

Figure 3A:
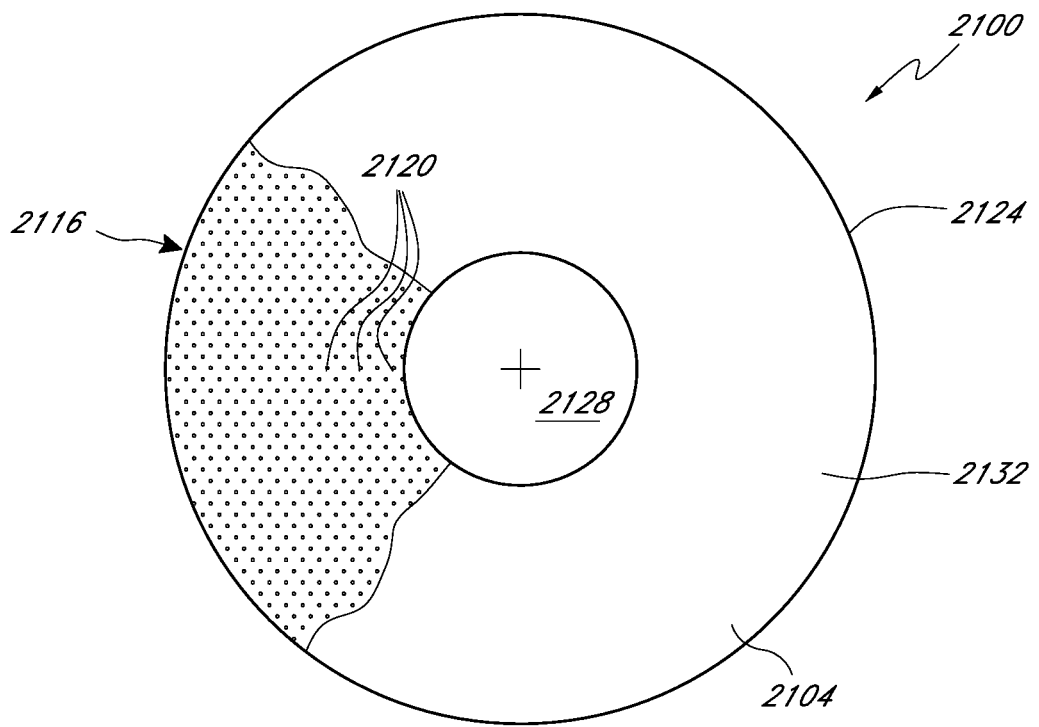
FIG. 3A is a top view of another embodiment of a mask configured to increase depth of focus.
Figure 3B:
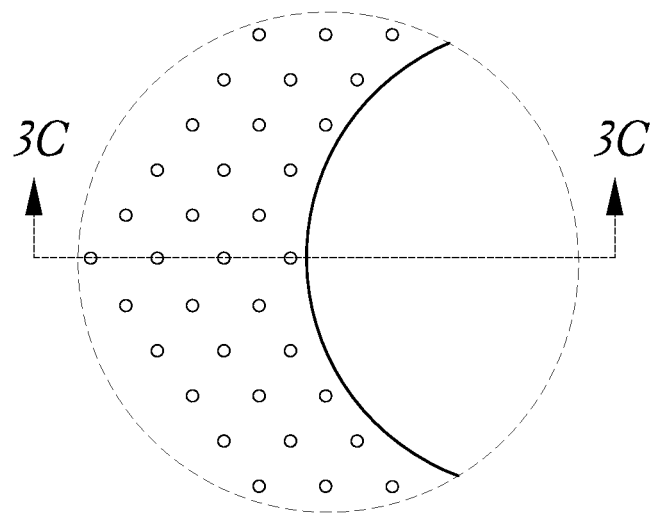
FIG. 3B is an enlarged view of a portion of the view of FIG. 3A.
Figure 3C:
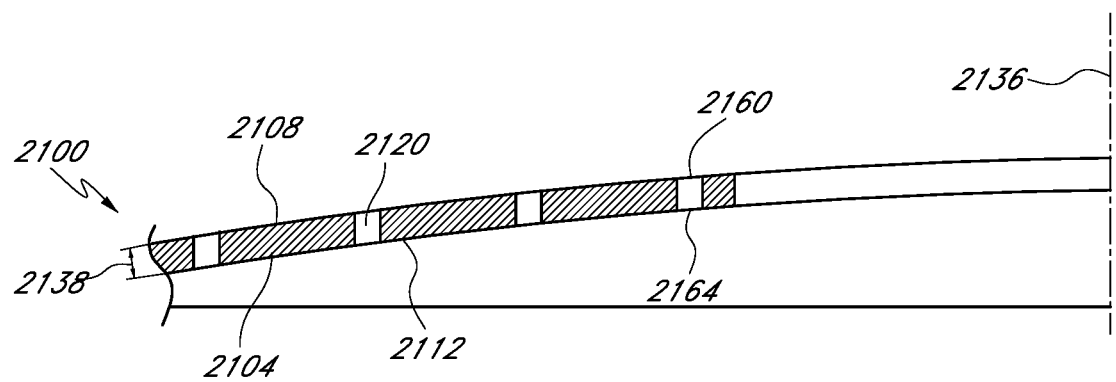
FIG. 3C is a cross-sectional view of the mask of FIG. 3B taken along line 3C-3C.

FIGS. 3-4 show another embodiment of a mask 2100 configured to increase depth of focus of an eye of a patient with presbyopia. The mask 2100 can be similar to the masks hereinbefore described, except as described differently below. The mask 2100 can be made of the materials discussed herein, including those discussed above. In addition, the mask 2100 can be formed by any suitable process. The mask 2100 can be configured to be applied to and/or embedded in an IOL.

In some embodiments, the mask 2100 can include a body 2104 that has an anterior surface 2108 and a posterior surface 2112. The body 2104 can be formed of any suitable material, including, but not limited to, at least one of an open cell foam material, an expanded solid material, and/or a substantially opaque material. In some embodiments, the material used to form the body 2104 can have relatively high water content. In some embodiments, the materials that can be used to form the body 2104 include polymers (e.g. PMMA, PVDF, polypropylene, polycarbonate, PEEK, polyethylene, acrylic copolymers (e.g., hydrophobic or hydrophilic), polystyrene, PVC, polysulfone), hydrogels, silicone, metals, metal alloys, or carbon (e.g., graphene, pure carbon).

In some embodiments, the mask 2100 can include a hole arrangement 2116. The hole arrangement 2116 can include a plurality of holes 2120. The holes 2120 are shown on only a portion of the mask 2100, but the holes 2120 can be located throughout the body 2104 in some embodiments. The mask 2100 can include an outer periphery 2124 that defines an outer edge of the body 2104. In some embodiments, the mask 2100 can include an aperture 2128 at least partially surrounded by the outer periphery 2124 and a non-transmissive portion 2132 located between the outer periphery 2124 and the aperture 2128.

The mask 2100 can be symmetrical, e.g., symmetrical about a mask axis 2136. In some embodiments, the outer periphery 2124 of the mask 2100 can be circular. The mask in general can have an outer diameter of at least about 3 mm and/or less than about 6 mm. In some embodiments, the mask is circular and can include a diameter of at least about 3 mm and/or less than or equal to about 4 mm. In some embodiments, the mask 2100 is circular and can include a diameter of about 3.2 mm.

In some embodiments, one of the anterior surface 2108 and the posterior surface 2112 of the body 2104 can be substantially planar. In some embodiments, very little or no uniform curvature can be measured across the planar surface. In some embodiments, both of the anterior and posterior surfaces 2108, 2112 can be substantially planar. In general, the thickness of the body 2104 of the mask 2100 can be within the range of from greater than zero to about 0.5 mm, about 1 micron to about 40 microns, in the range from about 5 microns to about 20 microns, or otherwise. In some embodiments, the body 2104 of the mask 2100 can include a thickness 2138 of at least about 5 microns and/or less than or equal to about 20 microns. In some embodiments, the body 2104 of the mask can include a thickness 2138 of at least about 5 microns and/or less than or equal to about 15 microns. In certain embodiments, the thickness 2138 can be about 15 microns, about 10 microns, about 8 microns, about 5 microns, or otherwise.

A substantially planar mask can have several advantages over a non-planar mask. For example, a substantially planar mask can be fabricated more easily than one that has to be formed to a particular curvature. In particular, the process steps involved in inducing curvature in the mask 2100 can be eliminated.

The aperture 2128 can be configured to transmit substantially all incident light along the mask axis 2136. The non-transmissive portion 2132 can surround at least a portion of the aperture 2128 and substantially prevent transmission of incident light thereon. As discussed in connection with the above masks, the aperture 2128 can be a throughhole in the body 2104 or a substantially light transmissive (e.g., transparent) portion thereof. The aperture 2128 of the mask 2100 can generally be defined within the outer periphery 2124 of the mask 2100. The aperture 2128 can take any of suitable configuration, such as those described above.

In some embodiments, the aperture 2128 can be substantially circular and can be substantially centered in the mask 2100. The size of the aperture 2128 can be any size that is effective to increase the depth of focus of an eye of a patient with presbyopia. In particular, the size of the aperture 2128 can be dependent on the location of the mask within the eye (e.g., distance from the retina). In some embodiments, the aperture 2128 can have a diameter of at least about 0.85 mm and/or less than or equal to about 2.2 mm. In certain embodiments, the diameter of the aperture 2128 is less than about 2 mm. In some embodiments, the diameter of the aperture is at least about 1.1 mm and/or less than or equal to about 1.6 mm. In some embodiments, the diameter of the aperture is at least about 1.3 mm and/or less than or equal to about 1.4 mm.

The non-transmissive portion 2132 can be configured to prevent transmission of visible light through the mask 2100. For example, in some embodiments, the non-transmissive portion 2132 can prevent transmission of substantially all or at least a portion of the spectrum of the incident visible light. In some embodiments, the non-transmissive portion 2132 can be configured to prevent transmission of substantially all visible light, e.g., radiant energy in the electromagnetic spectrum that is visible to the human eye. The non-transmissive portion 2132 can substantially prevent transmission of radiant energy outside the range visible to humans in some embodiments.

As discussed above, preventing transmission of light through the non-transmissive portion 2132 can decrease the amount of light that reaches the retina and the fovea that would not converge at the retina and fovea to form a sharp image. As discussed above, the size of the aperture 2128 is such that the light transmitted therethrough generally converges at the retina or fovea. Accordingly, a much sharper image can be presented to the retina than would otherwise be the case without the mask 2100.

In some embodiments, the non-transmissive portion 2132 can prevent transmission of at least about 90 percent of incident light. In some embodiments, the non-transmissive portion 2132 can prevent transmission of at least about 95 percent of all incident light. The non-transmissive portion 2132 of the mask 2100 can be configured to be substantially opaque to prevent the transmission of light.

In some embodiments, the non-transmissive portion 2132 can transmit no more than about 5% of incident visible light. In some embodiments, the non-transmissive portion 2132 can transmit no more than about 3% of incident visible light. In some embodiments, the non-transmissive portion 2132 can transmit no more than about 2% of incident visible light. In some embodiments, at least a portion of the body 2104 is configured to be opaque to more than 99 percent of the light incident thereon.

As discussed above, the non-transmissive portion 2132 may be configured to prevent transmission of light without absorbing the incident light. For example, the mask 2100 could be made reflective or could be made to interact with the light in a more complex manner, as discussed in U.S. Pat. No. 6,554,424, issued Apr. 29, 2003, which is hereby incorporated by reference in its entirety.

As discussed above, the mask 2100 can include a plurality of holes 2120. When the mask is formed embedded in the lens body, the lens body can extend at least partially through the holes, thereby creating a bond (e.g. material "bridge") between the lens body on either side of the mask. Further disclosure regarding the material "bridge" can be found in U.S. Publication No. 2011/0040376, filed Aug. 13, 2010, which is hereby incorporated by reference in its entirety.

The holes 2120 of the mask 2100 shown in FIG. 3A can be located anywhere on the mask 2100. In some embodiments, substantially all of the holes are in one or more regions of a mask. The holes 2120 of FIG. 3A extend at least partially between the anterior surface 2108 and the posterior surface 2112 of the mask 2100. In some embodiments, each of the holes 2120 includes a hole entrance 2160 and a hole exit 2164. The hole entrance 2160 is located adjacent to the anterior surface 2108 of the mask 2100. The hole exit 2164 is located adjacent to the posterior surface 2112 of the mask 2100. In some embodiments, each of the holes 2120 extends the entire distance between the anterior surface 2108 and the posterior surface 2112 of the mask 2100. Further details about possible hole patterns are described in WO 2011/020074, filed Aug. 13, 2010, which is hereby incorporated by reference in its entirety.

In some embodiments, the mask 2100 can include an annular region near the outer periphery 2124 of the mask having no holes. In certain embodiments, there are no holes within 0.1 mm of the outer periphery 2124 of the mask 2100.

In some embodiments, the mask can include an annular region around the inner periphery of the mask having no holes. In certain embodiments, there are no holes within 0.1 mm of the aperture 2128.

In some embodiments, the holes 2120 each have a same diameter. In certain embodiments, the holes 2120 can include one or more different diameters. In some embodiments, the diameter of any single hole 2120 is at least about 0.01 mm and/or less than or equal to about 0.02 mm. In some embodiments, the diameter of the holes 2120 can include one or more of the following hole diameters: 0.010 mm, 0.013 mm, 0.016 mm, and/or 0.019 mm. In some embodiments, holes of different diameters are interspersed throughout at least a portion of the mask 2100. In some embodiments, the holes are interspersed at irregular locations throughout at least a portion of the mask 2100.

In some embodiments there are at least about 1000 holes and/or less than or equal to about 2000 holes. In some embodiments, there are at least about 1000 holes and/or less than or equal to about 1100 holes. In some embodiments, there are about 1040 holes. In some embodiments, there are an equal number of holes of each diameter. In some embodiments, the number of holes having each diameter is different.

In some embodiments, the holes are interspersed at irregular locations throughout at least a portion of the mask 2100. In some embodiments, holes of different diameters are evenly interspersed throughout at least a portion of the mask 2100. For example, the mask 2100 can include a plurality of non-overlapping hole regions. The sum of the surface area of the plurality of non-overlapping hole regions can equal to total surface area of the entire hole region of the mask. Each region of the plurality of regions can include a number of holes, each of the holes having a different diameter. The number of holes in each region can equal the number of different hole sizes in the entire hole region.

Figure 4A:
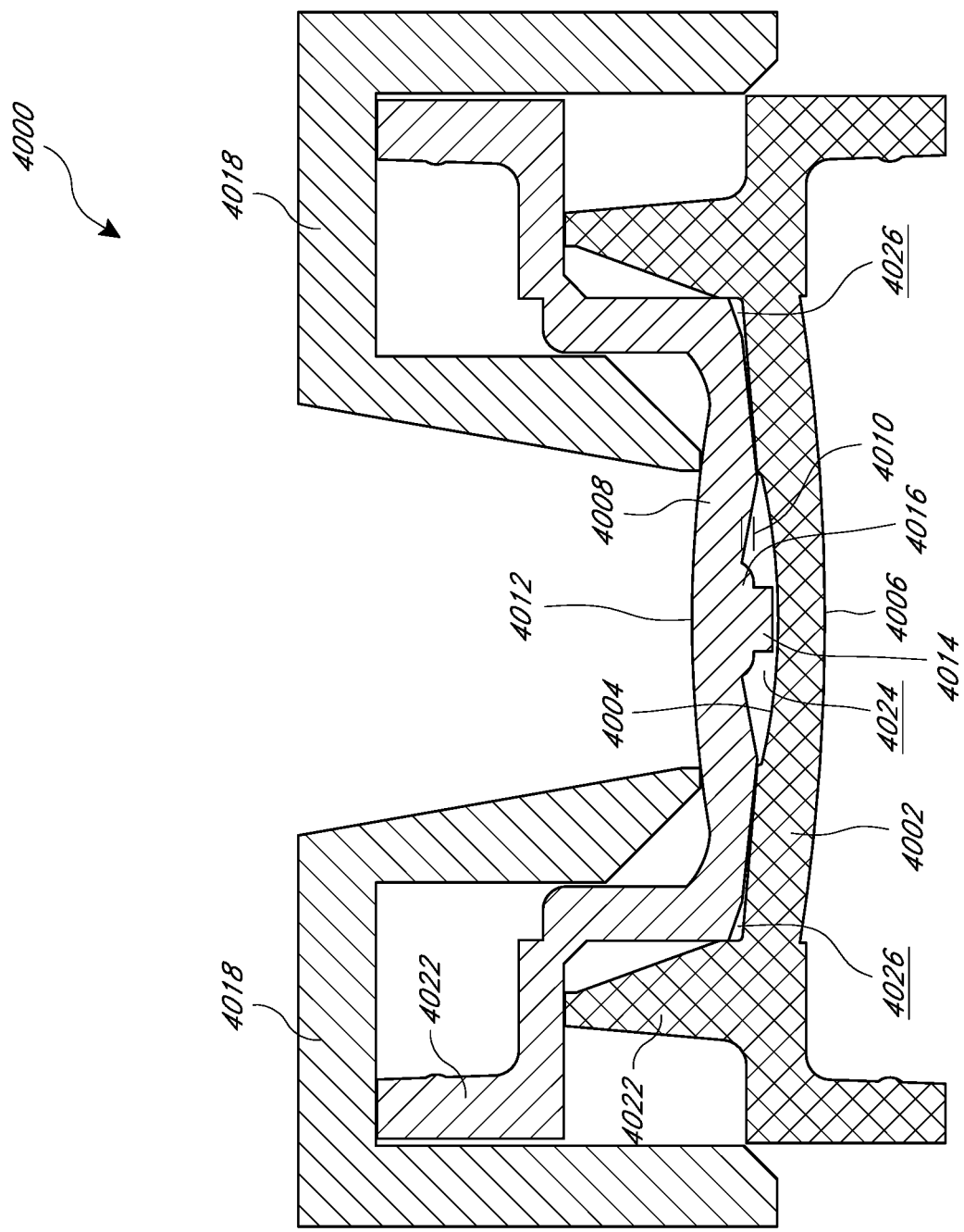
Figure 4B:
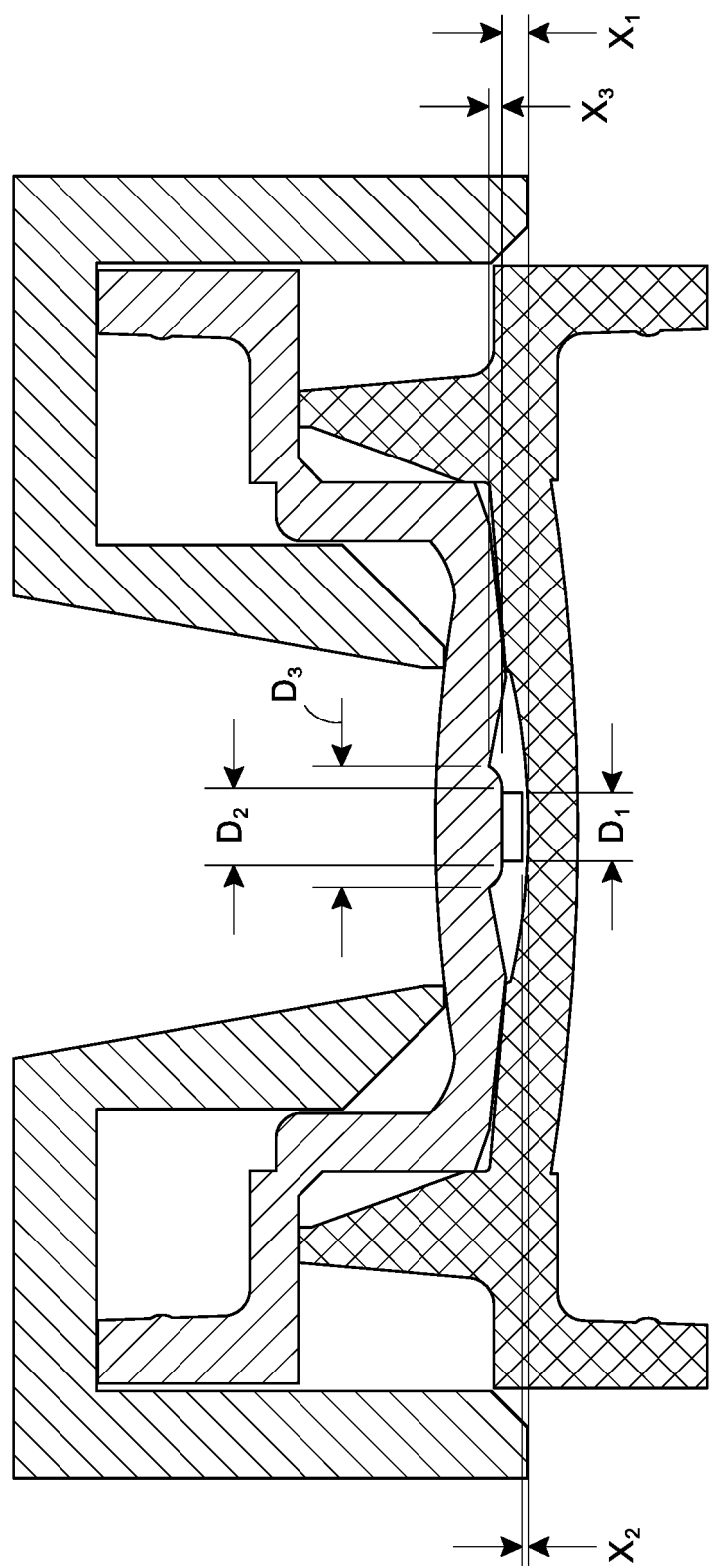

FIGS. 4A and 4B illustrate a cross section of a mold set 4000 having a first lens forming mold portion 4002, a second lens forming mold portion (not shown), a positioning mold portion 4008, and/or a haptic shield portion 4018. Each of the mold set components can be manufactured using any suitable technique, including, but not limited to, an injection molding technique. In some embodiments, multiple such mold sets 4000 can be combined into a mold assembly capable of manufacturing multiple lenses with embedded masks substantially simultaneously.

The first lens forming mold portion 4002 can include an interior lens forming surface 4004, an exterior surface 4006, a cavity 4024 for receiving lens material, and/or a haptic region 4026. The first lens forming mold portion 4002 can include an outer edge portion 4022 configured to join with the second lens forming mold portion and/or the positioning mold portion 4008.

The cavity 4024 can be sized for the dimensions of the intraocular lens. For example, the cavity 4024 can include a diameter of at least about 5 mm and/or less than or equal to about 6.5 mm. In certain embodiments, the cavity 4024 can include a diameter of about 6.0 mm. The diameter of the area including the cavity 4024 and the haptic region 4026 can be at least about 10 mm and/or less than or equal to about 20 mm. In certain embodiments, the diameter of the area including the cavity 4024 and the haptic region 4026 can be about 13.4 mm.

Figure 4D:
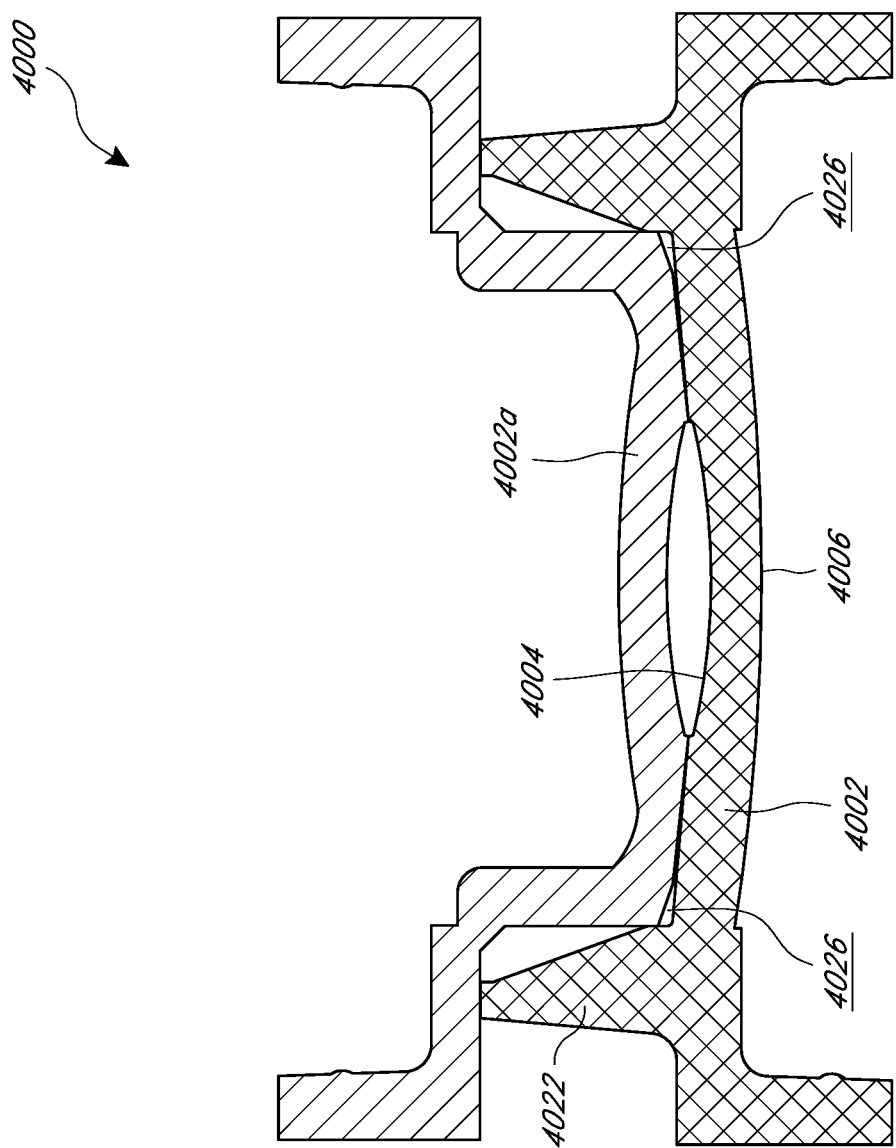

As shown in FIG. 4D, the second lens forming mold portion 4002a can be substantially similar, but complementary, to the first lens forming mold portion 4002 and can include a cavity for receiving lens material and/or a haptic region. The second lens forming mold portion 4002a can include an outer edge portion configured to join with the outer edge portion 4022 of the first lens forming mold portion 4002. When the second lens forming mold portion 4002a is joined with the first lens forming mold portion 4002, they constitute a lens mold. The specific shapes, sizes, and surfaces of the first and second lens forming mold portions can be designed to fabricate a lens of a desired shape and size.

The positioning mold portion 4008 can include an outer edge portion 4020 configured to join with the outer edge portion 4022 of the first lens forming mold portion 4002. The positioning mold portion 4008 can include an interior surface 4010 and an exterior surface 4012. The interior surface can include a protruding portion 4014, such as a protruding pin, extending from the interior surface 4010 of the positioning mold portion 4008. The protruding pin 4014 can include a shoulder portion 4016 with an enlarged diameter where the protruding pin 4014 extends from the interior surface 4010 of the positioning mold portion 4008. An annular mask 4028, such as those described herein, can be loaded onto the protruding pin 4014 before the positioning mold portion 4008 and the first lens forming mold portion 4002 are joined. The protruding pin 4014 can be transversely centered in the cavity 4024 to control the x-y position of the annular mask 4028 within the intraocular lens, while the shoulder portion 4016 can be configured to control the depth of the annular mask 4028 within the intraocular lens.

As shown in FIG. 4B, the end portion of the protruding pin 4014 can include a diameter $D_1$. The diameter $D_1$ can substantially correspond to an internal diameter of the annular mask 4028. For example, the diameter $D_1$ of the end portion of the protruding pin 4014 can be within about 10 microns of the internal diameter of the annular mask 4028, or within about 5 microns of the internal diameter of the annular mask 4028. If the diameter $D_1$ is too small, the annular mask 4028 may not properly center in the intraocular lens along an x-y dimension, as there may be excessive play between the annular mask 4028 and the protruding pin 4014. If the diameter $D_1$ is too large, it may be difficult to separate the annular mask 4028 from the protruding pin 4014 when the positioning mold portion 4008 is removed because of too tight of a fit. In some embodiments, the diameter $D_1$ can be at least about 1.1 mm and/or less than or equal to about 1.6 mm. In some embodiments, the diameter $D_1$ can be at least about 1.3 mm and/or less than or equal to about 1.4 mm.

The protruding pin 4014 can have a length such that an end portion of the protruding pin 4014 is within a distance $X_2$ from the interior surface 4004 of the first lens forming mold portion 4002 when the positioning mold portion 4008 is joined to the first lens forming mold portion. In certain embodiments, $X_2$ can be less than or equal to about 0.3 mm, less than or equal to about 0.2 mm, or less than or equal to about 0.1 mm. In certain embodiments $X_2$ can be about 0.1 mm. In certain embodiments, the distance $X_1$ from a base of the protruding pin 4014 to the interior surface 4004 of the first lens forming mold portion 4002 can be less than or equal to about 0.7 mm, less than or equal to about 0.6 mm, less than or equal to about 0.5 mm, or less than or equal to about 0.4 mm. In certain embodiments, the distance $X_1$ can be about 0.5 mm. The length of the protruding pin 4014, from the shoulder portion 4016, can be equal to $X_1$ less $X_2$ ($X_1-X_2$). In certain embodiments, the length of the protruding pin 4014, from the shoulder portion 4016, can be at least about 0.2 mm and/or less than or equal to about 0.6 mm. In certain embodiments, the length of the protruding pin 4014, from the shoulder portion 4016, can be about 0.4 mm. It should be understood, however, that the specific dimensions of the protruding pin 4014 may depend upon various factors, including the design and optical power of the IOL.

The diameter of the shoulder portion 4016 can be larger than the inner diameter of the annular mask 4028, and can be configured to provide support for the annular mask 4028 and still allow a sufficient amount of lens material to flow behind the annular mask 4028. The lens material that flows behind the annular mask 4028 can polymerize and help stabilize the annular mask 4028 when the positioning mold portion 4008 is removed, as discussed further herein.

The shoulder portion 4016 can include a substantially uniform diameter or a varying diameter. As shown in FIGS. 4A and 4B, the shoulder portion 4016 can include generally rounded side portions and can include a base diameter $D_3$ that is greater than an end portion diameter $D_2$. Any portion of the shoulder portion 4016 can include a diameter within a range of at least about 1.5 mm and/or less than or equal to about 2.5 mm. In some embodiments the diameter $D_3$ can be at least about 1.5 mm and/or less than or equal to about 2.5 mm. In certain embodiments, the diameter $D_3$ can be at least about 2.0 mm and/or less than or equal to about 2.5 mm. In certain embodiments, the diameter $D_3$ can be about 2.1 mm. In some embodiments, $D_2$ can be at least about 1.5 mm and/or less than or equal to about 1.75 mm. In some embodiments, $D_2$ can be at least about 40% of the outer diameter of the annular mask 4028 and/or less than or equal to about 60% of the outer diameter of the annular mask 4028. In certain embodiments, $D_2$ can be about 50% of the outer diameter of the annular mask 4028. In some embodiments, the difference between the diameter $D_1$ of the end of the protruding pin 4014 and the diameter $D_2$ of the shoulder portion 4016 can be less than or equal to about 0.4 mm, less than or equal to about 0.2 mm, or otherwise.

The length $X_3$ of the shoulder portion 4016 can be configured to control the depth of the annular mask 4028 within the intraocular lens. In some embodiments, the length $X_3$ is designed such that the annular mask 4028 is left substantially centered in the finished intraocular lens along the longitudinal axis of the lens. In some embodiments, the shoulder portion 4016 can include a length $X_3$ of at least about 0.15 mm and/or less than or equal to about 0.35 mm. In certain embodiments, the length $X_3$ can be about 0.25 mm. It should be understood, however, that the specific dimensions of the shoulder portion 4016 may depend upon various factors, including the design and optical power of the IOL.

The first lens forming mold portion 4002 and the positioning mold portion 4008 can be joined together by, for example, lying one mold portion atop the other mold portion. In some embodiments, the haptic shield 4018 can be configured to join the positioning mold portion 4008 or the first lens forming mold portion 4002. The haptic shield 4018 can be configured to block light from entering a haptic region 4026 of the mold during a photo curing stage of the manufacturing process. In some scenarios, if multiple doses of lens material are added to the mold and at least partially photo cured at different stages of the process, it may be desirable to block light from entering the haptic region during at least part of the curing process because later added doses of uncured lens material can cause previously polymerized lens material to swell and buckle. As shown in FIGS. 4A and 4B, the haptic shield 4018 can include a body portion positioned over the outer edge portions 4020, 4022 of the positioning mold portion 4008 and the first lens forming mold portion 4002. This configuration for the haptic shield 4018 can be used, for example, if curing light is provided on the positioning mold side of the assembly. FIG. 4C illustrates the haptic shield 4018 positioned over the first lens forming mold portion 4002 (the first lens forming mold portion is flipped compared to its orientation in FIGS. 4A and 4B). This configuration for the haptic shield 4018 can be used, for example, if curing light is provided on the first lens forming mold side of the assembly. In some embodiments, the mold set 4000 can include a support rack 4030. As shown in FIG. 4C, the support rack 4030 can include a first and a second stepped region 4032, 4034 configured to support the respective ones of the positioning mold portion 4008 and/or the haptic shield 4018.

Figure 5:
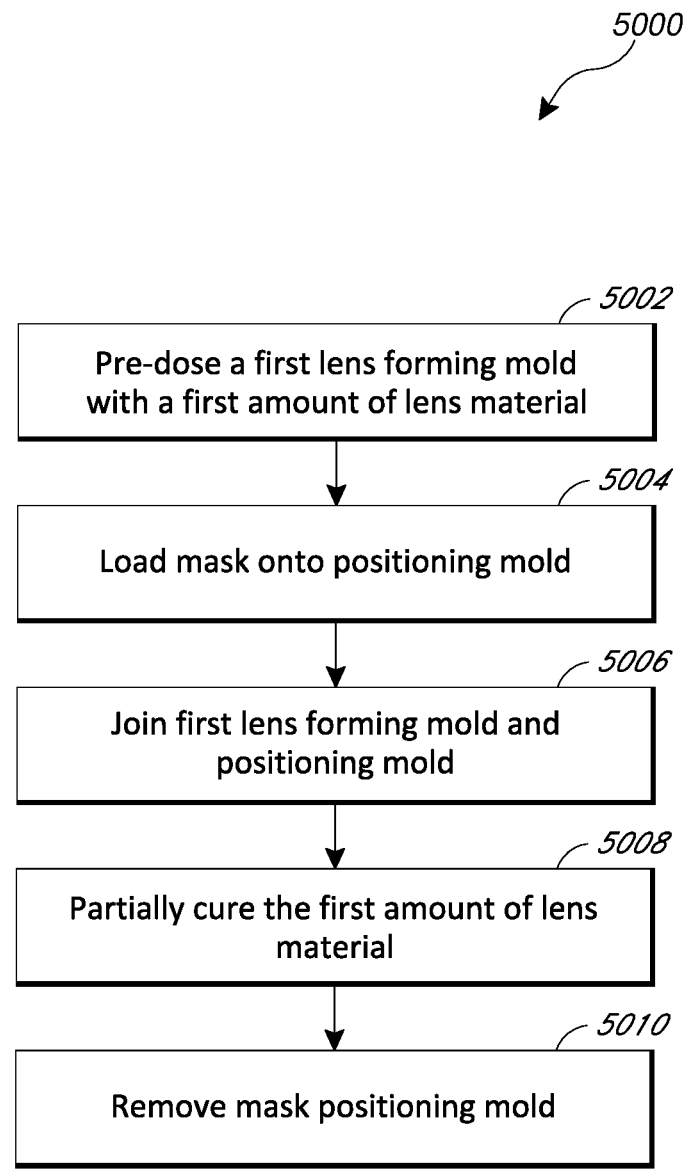
FIG. 5 is a flow chart illustrating an embodiment of a method for making an intraocular lens using the mold set illustrated in FIGS. 4A and 4B.
Figure 6:
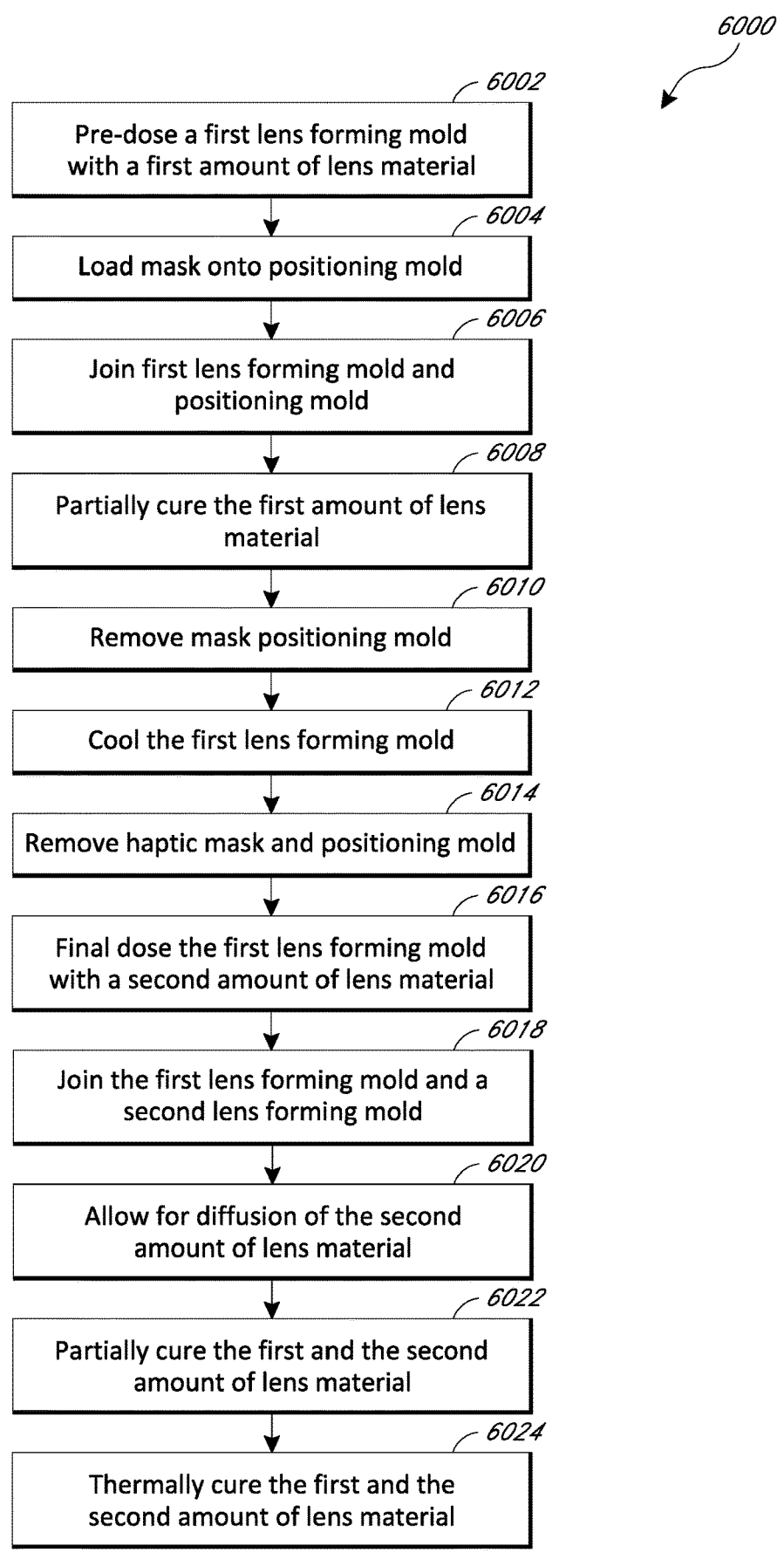
FIG. 6 is a flow chart illustrating another embodiment of a method for making an intraocular lens using the mold set illustrated in FIGS. 4A and 4B.

FIGS. 5 and 6 are flow charts illustrating methods of manufacturing the intraocular lens. The methods can be used to embed an annular mask within the intraocular lens and ensure the proper centration and depth of the annular mask in the intraocular lens. None of the method steps disclosed should be understood as necessarily being essential or indispensable unless otherwise stated, and either method can include additional manufacturing steps.

FIG. 5 illustrates a method 5000 of manufacturing an intraocular lens with an embedded annular mask using the mold set 4000 illustrated in FIGS. 4A and 4B. The method can include pre-dosing the first lens forming mold portion 4002 with a first amount of lens material (block 5002). The method can include loading the annular mask, including any of the annular masks described herein, onto the protruding pin 4014 of the positioning mold portion 4008 (block 5004). The method 5000 can include joining the first lens forming mold portion 4002 and the positioning mold portion 4008 (block 5006), and at least partially curing the first amount of lens material (block 5008). After partially curing the first amount of lens material, the positioning mold portion 4008 can be removed (block 5010), leaving the annular mask at least partially embedded in lens material. Aspects of each of these method steps are described in further detail in connection with FIG. 6.

FIG. 6 illustrates a method 6000 of manufacturing an intraocular lens with an embedded annular mask using the mold set 4000 illustrated in FIGS. 4A and 4B. The method can include pre-dosing a first lens forming mold portion 4002 with a first amount of lens material (block 6002). The lens material can include any of the lens materials described herein, including, but not limited to, the hydrophobic materials disclosed above.

In certain embodiments, the first amount of lens material can be equivalent to the amount of material necessary to completely fill the cavity 4024 and cause lens material to flow between the annular mask 4028 and the positioning mold portion 4008. In this way, the annular mask 4028 is at least partially embedded in lens material on both sides, which can aid in avoiding longitudinal movement of the annular mask 4028 when the first lens forming mold portion 4002 and the positioning mold portion 4008 are separated. If there is insufficient lens material to fill the cavity 4024, oxygen can be trapped in the mold, which can make it difficult to cure the material because oxygen can inhibit polymerization. In certain embodiments, the first amount of lens material can be at least about 100 microliters and/or less than or equal to about 150 microliters.

In some embodiments, the lens material can include an ultraviolet light absorber to protect the eye from ultraviolet light. The lens material can also include a light-sensitive initiator to allow the lens material to be photo cured by exposure to light. The light-sensitive initiator can include various biocompatible initiators, including, but not limited to, acylphosphine oxide initiators, such as Irgacure® 819. While the ultraviolet light absorption is a desirable feature of some embodiments of the intraocular lens, some light-sensitive initiators react to ultraviolet light. However, the presence of the ultraviolet light absorber could prevent such a light-sensitive initiator from being effective in a photo curing process. Thus, the initiator added to the lens material can be one that is activated when exposed to light having a wavelength outside the absorption spectrum of the ultraviolet light absorber (e.g., visible light range, violet-blue light range, or otherwise). In certain aspects, the initiator can be activated by light having a wavelength in a range from about 380 nm to about 495 nm. In certain aspects, the initiator can be activated by a light having a wavelength of about 420 nm. In certain aspects, the total amount of light initiator can be less than or equal to about 0.25% of the total amount of lens body material.

In block 6006, the first lens forming mold portion 4002 and the positioning mold portion 4008 can be joined together, for example, as shown in FIGS. 4A and 4B. In certain embodiments, the shoulder portion 4016 can be configured such that lens material can flow between a surface of the annular mask 4028 and the positioning mold portion 4008 when the mold portions 4002, 4008 are joined together. In some embodiments, before joining the mold portions 4002, 4008, excess lens material can be drained off.

In some embodiments, the haptic shield 4018 can be joined to the first lens forming mold portion 4002 and/or the positioning mold portion 4008 such that the haptic shield 4018 blocks light from reaching the haptic region 4026 and prevents polymerization of the lens material within the haptic region 4026 during certain curing stages of the fabrication process. In some embodiments, the haptic shield 4018 can join an outer edge portion 4020, 4022 of one or both of the mold portions 4002, 4008. The haptic shield 4018 can be positioned along the exterior surface 4012 of the positioning mold portion 4008 or the exterior surface 4006 of the first lens forming mold portion 4002. In certain embodiments the haptic shield 4018 can be configured to be embedded within one of the mold portions 4002, 4008 or can be positioned within the haptic region 4026.

After joining the mold portions 4002, 4008, the lens material can be at least partially cured (block 6010). For example, the lens material can be cured less than a full cure, e.g., at least about 10% and/or less than about 50% of a full monomer conversion. The lens material can be cured to a sufficient degree such that the annular mask 4028 remains with the first lens forming mold portion after removing the positioning mold portion. In addition, the partially cured lens material between the annular mask 4028 and the positioning mold portion 4008 can help hold the annular mask 4028 in place when the positioning mold portion 4008 is removed.

In some embodiments, the cure can be performed using a light cure, for example, using a 420 nm LED or any other suitable wavelength light described herein. Photo curing may be preferable to heat curing at this stage of the fabrication process because it can allow for greater control over the curing process. For example, a curing light can be turned on or off on command, which allows for fine control over the cure, whereas heat curing has more sluggish response times. In some embodiments, there can be a light intensity of at least about 0.5 milliwatts/cm$^2$ and/or less than or equal to about 10 milliwatts/cm$^2$. In some embodiments, the light intensity can be about 2 milliwatts/cm$^2$. In some embodiments, the partial curing can take place for less than about 10 minutes, less than about 6 minutes, less than about 5 minutes, or otherwise.

In some scenarios, the light can be applied to the positioning mold portion 4008. However, if the annular mask 4028 includes an ultraviolet light absorber, the annular mask 4028 can prevent ultraviolet light from reaching the lens material, thereby inhibiting the partial curing process. In some embodiments, the mold set 4000 can be flipped over before the partial curing process or otherwise configured such that the light can be applied to the first lens forming mold portion 4002 (which can be made from a material that is substantially transparent to the curing light).

After partially curing the lens material, at least the first lens forming mold portion 4002 can be cooled (block 6012). The cooling process can increase lens material adhesion to the first lens forming mold portion 4002 and/or stiffen the partially cured lens material to help ensure that the lens material and annular mask 4028 stay with the first lens forming mold portion 4002 when the positioning mold portion 4008 and/or haptic shield 4018 are removed (block 6014). In some embodiments, the cooling process can be used to cool the first lens forming mold portion 4002 by at least 20 degrees. In certain embodiments, the cooling process can be carried out using a cryogenic fluid, such as liquid nitrogen.

In some embodiments, the mold portions 4002, 4008 can be separated using a machine-operated process to ensure that the mold portions 4002, 4008 are vertically displaced without disrupting the position of the annular mask 4028.

The materials of the mold set 4000 can also be configured to help cause the annular mask 4028 to stay with the first lens forming mold portion 4002 when the positioning mold portion 4002 is removed. For example, the first lens forming mold portion 4002 can include a material that adheres to the lens material to a greater extent, and the positioning mold portion 4008 can include a material that releases the lens material and/or annular mask 4028 more easily. In certain embodiments, the first lens forming mold portion 4002 can include a resin.

When the positioning mold portion 4008 is removed, the protruding pin 4014 can leave behind a void that is substantially free of any lens material. This void can be filled with uncured lens material when the second amount of lens material is added. The void left by the protruding pin 4014 is in the region of the optical axis of the lens and extends to a depth near or at the interior lens forming surface 4004 of the first lens forming mold portion 4002. Since the volume substantially surrounding the optical axis of the lens is filled with only the second amount of lens material, the finished optic can include a homogeneous optical material in the optical zone.

After removing the positioning mold portion 4008 and/or the haptic shield 4018, a second amount of lens material can be added to the first lens forming mold portion 4002 and/or the second lens forming mold portion (block 6016), and the first lens forming mold portion and the second lens forming mold portion can be joined together (6018). In some embodiments, the second amount of lens material is sufficient to completely fill the volume between the first and second lens forming mold portions. In certain embodiments, the second amount of lens material can be at least about 100 microliters and/or less than or equal to about 150 microliters. In certain embodiments, the second amount of lens material is about 150 microliters. After joining the first and second lens forming mold portions, the second amount of lens material can be allowed to diffuse through the partially cured first amount of lens material for a period of time (block 6020).

Following the diffusion period, the first and the second amount of lens material can be at least partially cured (block 6022). The first and the second amount of lens material can be cured at least about 10% and/or less than about a 50% of a full conversion of monomer to polymer. The partial curing process helps stabilize the position of the annular mask 4028 before the final cure. In some embodiments, the cure is performed using a light cure, for example, using a 420 nm LED or any other suitable wavelength light described herein. In some embodiments, the light intensity can be at least about 0.5 milliwatts/cm$^2$ and/or less than or equal to about 10 milliwatts/cm$^2$. In some embodiments, the light intensity can be about 2 milliwatts/cm$^2$. In some embodiments, the light curing process can take place for less time than the first partial curing (block 6010). In some embodiments, the light intensity can be applied for less than about 5 minutes, less than about 3 minutes, or otherwise.

The final curing process can be carried out using thermal curing (block 6024). After the final cure, in some embodiments, the amount of leftover residual monomer can be less than 5% of the total amount of lens material, less than 1% of the total amount of lens material, less than 0.5% of the total amount of lens material, or otherwise, such that the residual monomer does not need to be extracted. In certain embodiments, only about 0.3% of residual monomer remains after the final cure.

After the final curing process, the intraocular lens can be hydrated with saline solution. As described above, the lens material can include a hydrophobic material. Hydrophobic lens materials can be useful because a finished lens may take up less water when hydrated in saline solution than lenses made of hydrophilic materials. If the lens body were to take up too much water, the lens body could swell and disrupt the positioning of the mask and/or damage the mask embedded within the intraocular lens. In certain embodiments, the intraocular lens material can include a water content of less than about 4%, or less than about 3%. In certain embodiments, the intraocular lens material can include a water content of about 2.5%.

In some embodiments, after the lens is removed from the mold set, it can be machined on either side or on both sides. For example, one side can be cut to the proper shape and then both sides can be polished. In some embodiments, the side of the lens to be cut is the side formed by the second lens forming mold portion.

Various embodiments have been described above. Although the invention has been described with reference to these specific embodiments, the descriptions are intended to be illustrative and are not intended to be limiting. Various modifications and applications may occur to those skilled in the art without departing from the true spirit and scope of the invention as defined in the appended claims.

What is claimed is:

1. A method of manufacturing an intraocular lens, the method comprising:
    adding a first amount of a lens material to a first mold portion;
    positioning a mask with an aperture on a shoulder portion of a protruding pin of a positioning mold portion, the shoulder portion configured to control a depth of the mask in the intraocular lens;
    joining the first mold portion and the positioning mold portion; and
    partially curing the first amount of the lens material.

2. The method of claim 1, wherein a diameter of the shoulder portion is larger than a diameter of the aperture of the mask.

3. The method of claim 1, wherein the shoulder portion extends from an interior surface of the positioning mold portion.

4. The method of claim 1, wherein joining the first mold portion and the positioning mold portion causes lens material to flow into a space between a surface of the mask and an inner surface of the positioning mold portion so as to at least partially surround the mask with lens material on both of its sides.

5. The method of claim 1, wherein the lens material comprises an ultraviolet light absorber and a light-sensitive initiator, the light-sensitive initiator being configured to cure the lens material when exposed to light having a wavelength outside the absorption spectrum of the ultraviolet light absorber.

6. The method of claim 5, wherein the light-sensitive initiator is configured to be activated by light having a wavelength in a range from about 380 nm to about 495 nm.

7. The method of claim 1, wherein partially curing the first amount of the lens material comprises applying light to the first mold portion.

8. The method of claim 1, wherein partially curing the first amount of the lens material comprises curing the first amount of the lens material to a sufficient degree that the mask remains with the first mold portion after removing the positioning mold portion.

9. The method of claim 1, further comprising cooling the first mold portion.

10. The method of claim 9, wherein cooling the first mold portion comprises cooling the first mold portion using a cryogenic fluid.

11. The method of claim 9, wherein cooling the first mold portion comprises reducing a temperature of the first mold portion by at least 20 degrees.

12. The method of claim 1, further comprising removing the positioning mold portion and joining the first mold portion and a second mold portion.

13. The method of claim 12, further comprising adding a second amount of the lens material to the second mold portion.

14. The method of claim 13, further comprising partially curing the second amount of the lens material by exposure to light.

15. The method of claim 14, further comprising, after partially curing the second amount of the lens material by exposure to light, thermally curing the second amount of the lens material.

16. The method of claim 15, further comprising polymerizing at least 99% of the first and second amounts of the lens material.

17. The method of claim 1, wherein the lens material is a hydrophobic material.

18. The method of claim 1, further comprising joining a haptic shield and the positioning mold such that the haptic shield prevents polymerization of the lens material in a haptic region.

* * * * *